United States Patent
Lawson et al.

(10) Patent No.: US 11,760,723 B2
(45) Date of Patent: Sep. 19, 2023

(54) METHOD OF PREPARING A DON PRODRUG FROM L-PYROGLUTAMIC ACID

(71) Applicant: DRACEN PHARMACEUTICALS, INC., New York, NY (US)

(72) Inventors: Jon Philip Lawson, Wildwood, MO (US); Robert Christian Wild, Murrieta, CA (US); Yiyang Shao, Beijing (CN); Jinxiao Chu, Beijing (CN); Jinchao Weng, Beijing (CN); Pavel Majer, Sykesville, MD (US)

(73) Assignee: Dracen Pharmaceuticals, Inc., Washington, DC (US)

( * ) Notice: Subject to any disclaimer, the term of this patent is extended or adjusted under 35 U.S.C. 154(b) by 83 days.

(21) Appl. No.: 17/430,285

(22) PCT Filed: Feb. 11, 2020

(86) PCT No.: PCT/US2020/017748
§ 371 (c)(1),
(2) Date: Aug. 11, 2021

(87) PCT Pub. No.: WO2020/167829
PCT Pub. Date: Aug. 20, 2020

(65) Prior Publication Data
US 2022/0194898 A1    Jun. 23, 2022

(30) Foreign Application Priority Data
Feb. 11, 2019   (WO) ................ PCT/CN2019/074800

(51) Int. Cl.
C07D 209/20   (2006.01)
C07C 249/02   (2006.01)
C07D 207/28   (2006.01)

(52) U.S. Cl.
CPC .......... *C07D 209/20* (2013.01); *C07C 249/02* (2013.01); *C07D 207/28* (2013.01); *C07B 2200/13* (2013.01)

(58) Field of Classification Search
CPC .. C07D 209/20; C07C 249/02; C07B 2200/13
See application file for complete search history.

(56) References Cited

U.S. PATENT DOCUMENTS

| | | |
|---|---|---|
| 10,336,778 B2 | 7/2019 | Slusher et al. |
| 10,568,868 B2 | 2/2020 | Slusher et al. |
| 10,738,066 B2 | 8/2020 | Slusher et al. |
| 10,842,763 B2 | 11/2020 | Slusher et al. |
| 10,954,257 B2 | 3/2021 | Slusher et al. |
| 2018/0221337 A1 | 8/2018 | Slusher et al. |
| 2018/0221395 A1 | 8/2018 | Slusher et al. |
| 2018/0222930 A1 | 8/2018 | Slusher et al. |
| 2019/0315783 A1 | 10/2019 | Slusher et al. |
| 2019/0315784 A1 | 10/2019 | Slusher et al. |
| 2022/0089522 A1 | 3/2022 | Lawson et al. |

FOREIGN PATENT DOCUMENTS

| | | |
|---|---|---|
| WO | WO-2017023774 A1 | 2/2017 |
| WO | WO-2017023787 A1 | 2/2017 |
| WO | WO-2017023791 A1 | 2/2017 |
| WO | WO-2017023793 A2 | 2/2017 |
| WO | WO-2019071110 A1 | 4/2019 |
| WO | WO-2020167831 A1 | 8/2020 |

OTHER PUBLICATIONS

Ahluwalia, G.S., et al., "Metabolism and action of amino acid analog anti-cancer agents," *Pharmacology and Therapeutics* 46(2):243-271, Elsevier (1990).
Bitta, J., and Kubik, S., "Cyclic hexapeptides with free carboxylate groups as new receptors for monosaccharides," *Organic Letters* 3(17):2637-2640, American Chemical Society (2001).
Hobbs, M.J., et al., "Elevation of Endogenous Nucleophiles in Rat Lung by Cysteine and Glutathione Esters In Vitro," *Biochemical Pharmacology* 55:1573-1584, Elsevier (1998).
International Search Report and Written Opinion for International Application No. PCT/US2020/17748, U.S. Patent and Trademark Office, Alexandria, VA., dated Apr. 29, 2020.
Lynch, G., et al., "Phase II evaluation of DON (6-diazo-5-oxo-L-norleucine) in patients with advanced colorectal carcinoma," *American Journal of Clinical Oncology* 5(5):541-543, Lippincott Williams & Wilkins (1982).
Moss, G.P., "Basic Terminology of Stereochemistry," *Pure & Appl. Chem.* 68:2193-2222, International Union of Pure and Applied Chemistry, Walter de Gruyter (1996).
Rosenfeld, H., and Roberts, J., "Enhancement of Antitumor Activity of Glutamine Antagonists 6-Diazo-5-oxo-L-norleucine and Acivicin in Cell Culture by Glutaminase-Asparaginase," *Cancer Research* 41:1324-1328, American Association for Cancer Research (1981).

*Primary Examiner* — Kamal A Saeed
(74) *Attorney, Agent, or Firm* — Sterne, Kessler, Goldstein & Fox P.L.L.C.

(57) ABSTRACT

The present disclosure provides a method of preparing a compound of Formula I, wherein $R^1$ is $C_1$-$C_4$ alkyl; $R^2$ is C1-C4 alkyl; and $R^3$ is selected from the group consisting of $C_1$-$C_6$ alkyl, (aryl)alkyl, and (heteroaryl)alkyl in >95% chemical purity and >95% enantiomeric excess.

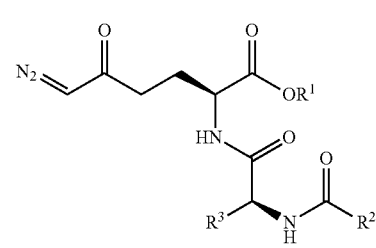

I

20 Claims, 8 Drawing Sheets

METHOD OF PREPARING A DON PRODRUG FROM L-PYROGLUTAMIC ACID

BACKGROUND OF THE INVENTION

6-Diazo-5-oxo-L-norleucine (DON) is a glutamine antagonist that exhibits promising activity in preclinical models to treat a variety of diseases such as cancer. See, e.g., Ahluwalia et al., *Pharmac The.* 46:243-371 (1990). But the clinical development of DON has been hampered by its dose-limiting toxicity in humans, especially in the intestinal epithelium. See, e.g., Rosenfeld and Roberts, *Cancer Research* 41:1324-1328 (1981) and Lynch et al., *Am J Clin Oncol* (CCT) 5:541-543 (1982). Administering DON as a prodrug may help mitigate this toxicity.

WO 2017/023774 discloses isopropyl (S)-2-((S)-2-acetamido-3-(1H-indol-3-yl)propanamido)-6-diazo-5-oxohexanoate and other prodrugs of DON, and methods to make these prodrugs. DON prodrugs can be used to treat cancer, cognitive deficits, metabolic reprogramming disorders, and other diseases. See WO 2017/023793, WO 2017/023791, and WO 2017/023787.

There exists a need for improved methods to prepare DON prodrugs. Isopropyl (S)-2-amino-6-diazo-5-oxohexanoate and ethyl (S)-2-amino-6-diazo-5-oxohexanoate are putative synthetic intermediates that can be used in this process. But these compounds cyclize under mild conditions to give isopropyl (S)-5-(diazomethyl)-3,4-dihydro-2H-pyrrole-2-carboxylate and ethyl (S)-5-(diazomethyl)-3,4-dihydro-2H-pyrrole-2-carboxylate, respectfully. See WO 2017/023774. The chemical instability of isopropyl (S)-2-amino-6-diazo-5-oxohexanoate and ethyl (S)-2-amino-6-diazo-5-oxohexanoate limits their usefulness as synthetic intermediates, especially in large-scale syntheses that may require reaction conditions that are incompatible with their propensity to cyclize and/or decompose by other mechanisms.

BRIEF SUMMARY OF THE INVENTION

Applicant has unexpectedly found that isopropyl (S)-2-((S)-2-acetamido-3-(1H-indol-3-yl)propanamido)-6-diazo-5-oxohexanoate can be obtained in high chemical purity and in high enantiomeric excess by reacting isopropyl (S)-2-amino-6-diazo-5-oxohexanoate with acetyl-L-tryptophan in the presence of ethyl cyano(hydroxyimino)acetate and a carbodiimide, e.g., N,N'-dicyclohexylcarbodiimide (DCC), N,N'-diisopropylcarbodiimide or N-(3-dimethylaminopropyl)-N'-ethylcarbodiimide hydrochloride (EDC).

In one aspect, the disclosure provides a method of preparing a compound of Formula I:

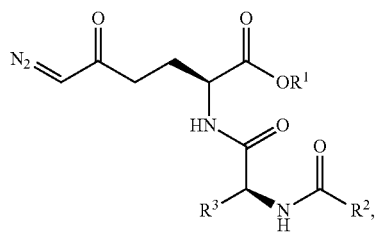

wherein $R^1$ is $C_1$-$C_4$ alkyl; $R^2$ is $C_1$-$C_4$ alkyl; and $R^3$ is selected from the group consisting of $C_1$-$C_6$ alkyl, (aryl)alkyl, and (heteroaryl)alkyl.

In another aspect, the disclosure provides a method of preparing a compound of Formula I in >95% chemical purity and >95% enantiomeric excess.

In another aspect, the disclosure provides a method of preparing isopropyl (S)-2-((S)-2-acetamido-3-(1H-indol-3-yl)propanamido)-6-diazo-5-oxohexanoate in >95% chemical purity and >95% enantiomeric excess.

In another embodiment, the disclosure provides a crystalline form of (S)-2-((S)-2-acetamido-3-(1H-indol-3-yl)propanamido)-6-diazo-5-oxohexanoate.

DETAILED DESCRIPTION OF THE INVENTION

Figure 1:
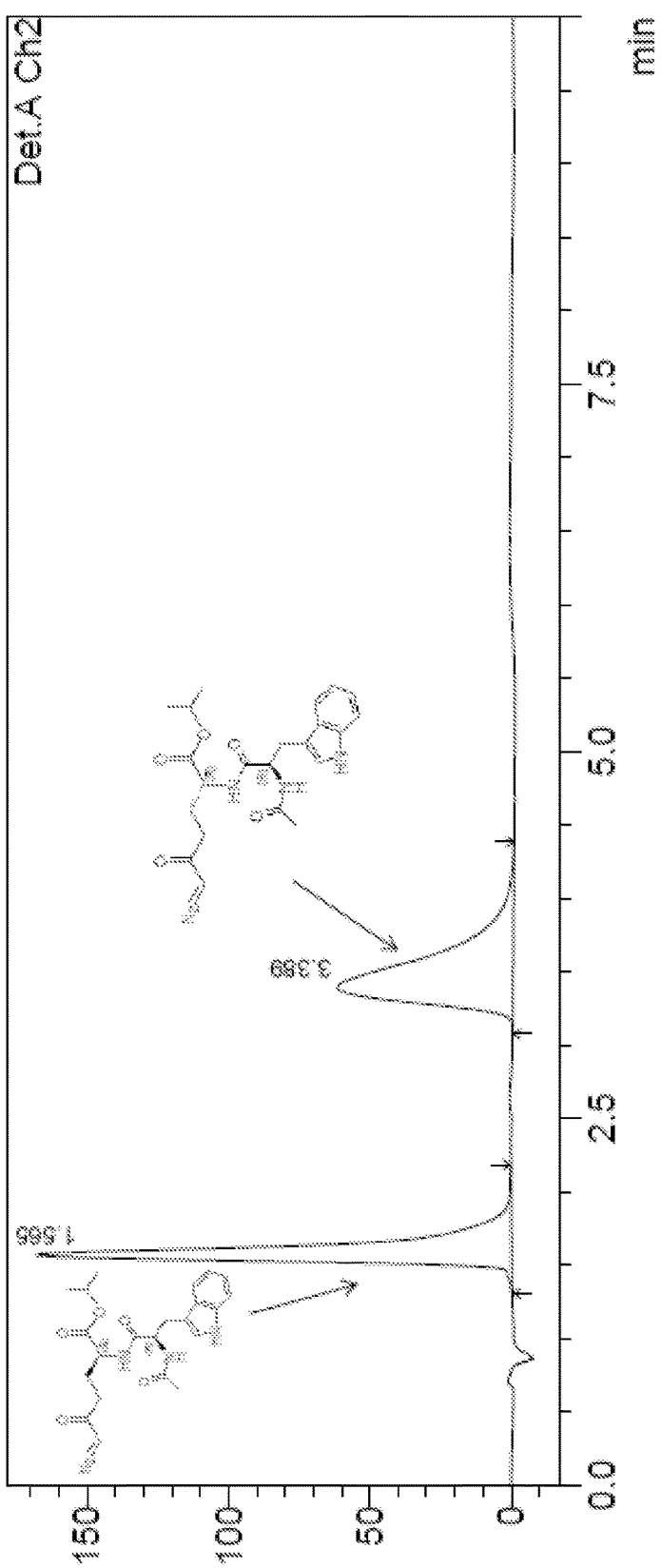
FIG. 1 is a chiral HPLC chromatogram showing the chiral resolution of a sample containing isopropyl (S)-2-((R)-2-acetamido-3-(1H-indol-3-yl)propanamido)-6-diazo-5-oxohexanoate and isopropyl (R)-2-((R)-2-acetamido-3-(1H-indol-3-yl)propanamido)-6-diazo-5-oxohexanoate.

In one embodiment, the disclosure provides a method of preparing a compound of Formula I:

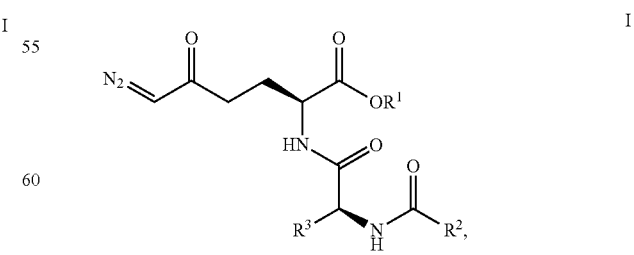

wherein $R^1$ is $C_1$-$C_4$ alkyl; $R^2$ is $C_1$-$C_4$ alkyl; and $R^3$ is selected from the group consisting of $C_1$-$C_6$ alkyl, (aryl)alkyl, and (heteroaryl)alkyl, the method comprising:

reacting a compound of Formula II:

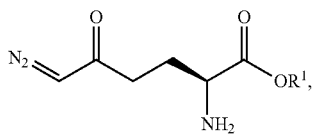

wherein $R^1$ is $C_1$-$C_4$ alkyl, with a compound of Formula III:

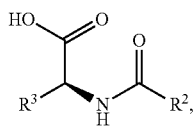

wherein $R^2$ is $C_1$-$C_4$ alkyl; and $R^3$ is selected from the group consisting of $C_1$-$C_6$ alkyl, (aryl)alkyl, and (heteroaryl)alkyl, in a solvent in the presence of an alkyl cyano(hydroxyimino)acetate, or a salt thereof, a carbodiimide, and a base, at a temperature of about 0° C. to about 40° C.

In another embodiment in connection with the preparation of the compound of Formula I, the method further comprises isolating the compound of Formula I.

In another embodiment in connection with the preparation of the compound of Formula I, the method further comprises isolating the compound of Formula I by column chromatography on silica gel. In another embodiment, the eluent comprises methanol. In another embodiment, the eluent comprises dichloromethane.

In another embodiment in connection with the preparation of the compound of Formula I, the method further comprises isolating the compound of Formula I by recrystallization in a recrystallization solvent. The recrystallized product may be collected using any method known in the art, e.g., by filtration or centrifugation. In another embodiment, the recrystallization solvent comprises methanol. In another embodiment, the recrystallization solvent comprises dichloromethane.

In another embodiment in connection with the preparation of the compound of Formula I, the solvent is selected from the group consisting of tetrahydrofuran, N,N-dimethylformamide (DMF), N-methyl-2-pyrrolidinone (NMP), dimethylacetamide (DMAc), dichloromethane (DCM), tetrahydrofuran, 2-methyltetrahydrofuran, and dioxane. In another embodiment, the solvent is N,N-dimethylformamide.

In another embodiment in connection with the preparation of the compound of Formula I, the carbodiimide is N,N'-diisopropylcarbodiimide or N,N'-dicyclohexylcarbodiimide. In another embodiment, the carbodiimide is N,N'-dicyclohexylcarbodiimide.

In another embodiment in connection with the preparation of the compound of Formula I, the alkyl cyano(hydroxyimino)acetate is ethyl cyano(hydroxyimino)acetate. Ethyl cyano(hydroxyimino)acetate is also known as Oxyma-Pure®. In another embodiment the alkyl cyano(hydroxyimino)acetate is ethyl (hydroxyimino) cyanoacetate potassium salt. Ethyl (hydroxyimino)cyanoacetate potassium salt is also known as K-OxymaPure®.

In another embodiment in connection with the preparation of the compound of Formula I, the base is 2,4,6-trimethylpyridine.

In another embodiment in connection with the preparation of Formula I, the temperature is about 0° C. to about 40° C.

In another embodiment in connection with the preparation of the compound of Formula I, the stereomutation of a compound of Formula II is less than about 2%. In another embodiment, the stereomutation of a compound having Formula II is less than about 1%.

In another embodiment in connection with the preparation of the compound of Formula I, the stereomutation of a compound of Formula III is less than about 2%. In another embodiment, the stereomutation of a compound having Formula III is less than about 1%.

In another embodiment in connection with the preparation of the compound of Formula I, the compound of Formula I is obtained in about 95% ee or more (as determined by chiral HPLC). In another embodiment, the compound of Formula I is obtained in about 96% ee or more. In another embodiment, the compound of Formula I is obtained in about 97% ee or more. In another embodiment, the compound of Formula I is obtained in about 98% ee or more. In another embodiment, the compound of Formula I is obtained in about 99% ee or more. In another embodiment, the compound of Formula I is obtained in 99.5% ee or more. In another embodiment, the compound of Formula I is obtained in 99.8% ee or more.

In another embodiment in connection with the preparation of the compound of Formula I, the compound of Formula I is obtained in a chemical purity (as determined by HPLC) of about 95% or more. In another embodiment, the compound of Formula I is obtained in a chemical purity of about 96% or more. In another embodiment, the compound of Formula I is obtained in a chemical purity of about 97% or more.

In another embodiment, the compound of Formula I is obtained in a chemical purity of about 98% or more. In another embodiment, the compound of Formula I is obtained in a chemical purity of about 99% or more.

In another embodiment in connection with the preparation of the compound of Formula I, the compound of Formula I is obtained in a chemical yield of about 50% or more. In another embodiment, the compound of Formula I is obtained in a chemical yield of about 55% or more. In another embodiment, the compound of Formula I is obtained in a chemical yield of about 60% or more. In another embodiment, the compound of Formula I is obtained in a chemical yield of about 65% or more. In another embodiment, the compound of Formula I is obtained in a chemical yield of about 70% or more. In another embodiment, the compound of Formula I is obtained in a chemical yield of about 75% or more. In another embodiment, the compound of Formula I is obtained in a chemical yield of about 80% or more. In another embodiment, the compound of Formula I is obtained in a chemical yield of about 85% or more. In another embodiment, the compound of Formula I is obtained in a chemical yield of about 90% or more. In another embodiment, the compound of Formula I is obtained in a chemical yield of about 95% or more.

In another embodiment in connection with the preparation of the compound of Formula I, Formula II, e.g., isopropyl (S)-2-amino-6-diazo-5-oxohexanoate, is used as a starting material in an amount of 100 g or more. In another embodiment, Formula II is used as a starting material in an amount of 250 g or more. In another embodiment, Formula II is used as a starting material in an amount of 500 g or more. In another embodiment, Formula II is used as a starting material in an amount of 1000 g or more.

In another embodiment, the disclosure provides a method of preparing a compound of Formula II:

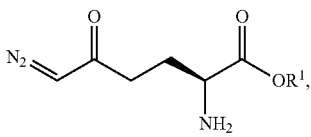

the method comprising reacting a compound of Formula IV:

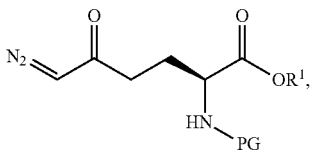

with a deprotecting agent in a solvent at a temperature of about −5° C. to about 30° C., wherein $R^1$ is $C_1$-$C_4$ alkyl; and PG is a protecting group.

In another embodiment in connection with the preparation of a compound of Formula II, the PG is selected from the group consisting of fluorenylmethyloxycarbonyl (Fmoc), carboxybenzyl (CBz), tert-butyloxycarbonyl (Boc), allyloxycarbonyl (Alloc), and methyl carbamate.

In another embodiment in connection with the preparation of a compound of Formula II, the PG is fluorenylmethyloxycarbonyl.

In another embodiment in connection with the preparation of a compound of Formula II, the deprotecting agent is selected from the group consisting of piperidine, diethylamine, triethylamine, and trimethylamine.

In another embodiment in connection with the preparation of a compound of Formula II, the solvent is selected from the group consisting of tetrahydrofuran, 2-methyltetrahydrofuran, and dichloromethane. In another embodiment, the solvent is dichloromethane.

In another embodiment in connection with the preparation of a compound of Formula II, the temperature is about 5° C. to about 15° C.

In another embodiment, the disclosure provides a method of preparing a compound of Formula IV:

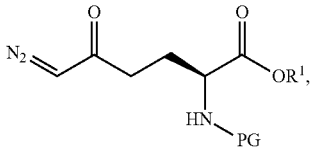

the method comprising reacting a compound of Formula V:

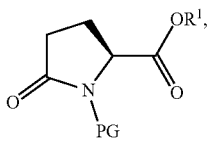

with a diazo reagent in the presence of an organolithium reagent in a solvent at a temperature of about −120° C. to about −40° C., wherein $R^1$ is $C_1$-$C_4$ alkyl; an PG is a protecting group.

In another embodiment in connection with the preparation of a compound of Formula IV, PG is selected from the group consisting of fluorenylmethyloxycarbonyl, carboxybenzyl, and tert-butyloxycarbonyl. In another embodiment, PG is fluorenylmethyloxycarbonyl.

In another embodiment in connection with the preparation of a compound of Formula IV, the diazo reagent is $(R^{4a})(R^{4b})(R^{4c})SiCHN_2$, wherein $R^{4a}$, $R^{4b}$, and $R^{4c}$ are each independently $C_1$-$C_4$ alkyl. In another embodiment, the diazo reagent is trimethylsilyldiazomethane.

In another embodiment in connection with the preparation of a compound of Formula IV, the organolithium reagent is a $C_1$-$C_6$ alkyl lithium. In another embodiment, the organolithium reagent is n-butyllithium or methyllithium.

In another embodiment in connection with the preparation of a compound of Formula IV, the solvent is selected from the group consisting of tetrahydrofuran, 2-methyltetrahydrofuran, hexane, and heptane, and mixtures thereof. In another embodiment, the solvent is tetrahydrofuran.

In another embodiment in connection with the preparation of a compound of Formula IV, wherein the temperature is about −90° C. to about −50° C. In another embodiment, the temperature is about −65° C.

In another embodiment in connection with the preparation of a compound of Formula IV, the organolithium reagent is added to mixture of the diazo reagent and a compound of Formula V in a solvent.

In another embodiment, the disclosure provides a method of preparing a compound of Formula V:

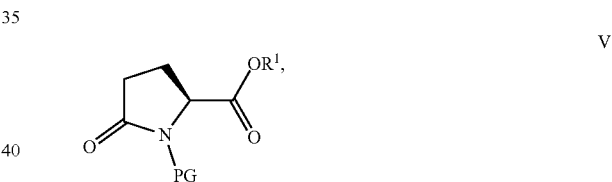

the method comprising reacting a compound of Formula VI:

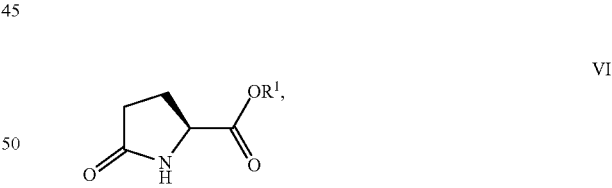

with compound of Formula VII:

PG-X    VII, in a solvent at a temperature of about −100° C. to about −60° C., wherein $R^1$ is $C_1$-$C_4$ alkyl; X is a leaving group, e.g., X is selected from the group consisting of —Cl, —Br, —I, —O-succinimide, —O-1,2,3-benzotriazole, and —O-aryl, e.g., pentafluorophenyl; and PG is a protecting group.

In another embodiment in connection with the preparation of a compound of Formula V, PG is selected from the group consisting of fluorenylmethyloxycarbonyl, carboxybenzyl, and tert-butyloxycarbonyl. In another embodiment, PG is fluorenylmethyloxycarbonyl.

In another embodiment in connection with the preparation of a compound of Formula V, the solvent is selected from the group consisting of tetrahydrofuran, 2-methyltetrahydrofuran, hexane, heptane, and dimethoxyethane. In another embodiment, the solvent is tetrahydrofuran.

In another embodiment in connection with the preparation of a compound of Formula V, the temperature is about −85° C. to about −75° C.

In another embodiment in connection with the preparation of a compound of Formula V, the reaction of a compound of Formula VI with Formula VII is carried out in the presence of a base, e.g., a lithium or magnesium base. In one embodiment, the base is lithium bis(trimethylsilyl)amide (LiHMDS).

In another embodiment, the disclosure provides a method of preparing a compound of Formula VI:

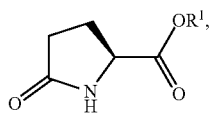

VI the method comprising reacting L-pyroglutamic acid with $R^1OH$, wherein $R^1$ is $C_1$-$C_4$ alkyl.

In another embodiment in connection with the preparation of a compound of Formula VI, the reacting is carried out in the presence of 1,1'-carbonyldiimidazole (CDI) or a carbodiimide at a temperature of about 5° C. to about 50° C. In another embodiment, the carbodiimide is N,N'-diisopropylcarbodiimide or N,N'-dicyclohexylcarbodiimide.

In another embodiment in connection with the preparation of a compound of Formula VI, the reacting is carried out in the presence of an acid at a temperature of about 25° C. to about 100° C. In another embodiment, the acid is selected from the group consisting of p-toluenesulfonic acid, methane sulfonic, acid, benzene sulfonic acid, sulfonic acid resins, sulfuric acid, and hydrochloric acid. In another embodiment, the acid is p-toluenesulfonic acid. In another embodiment, the temperature is about 80° C.

In another embodiment, the disclosure provides a method of preparing Formulae I, II, IV, V, or VI, wherein $R^1$ is isopropyl.

In another embodiment, the disclosure provides a method of preparing Formula I, wherein $R^2$ is methyl.

In another embodiment, the disclosure provides a method of preparing Formula I, wherein $R^3$ is selected from the group consisting of:

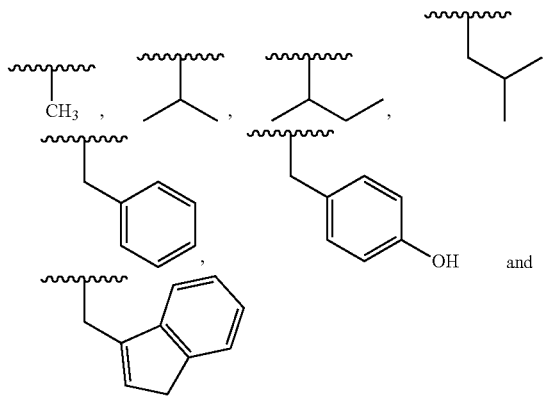

and

In another embodiment, $R^3$ is:

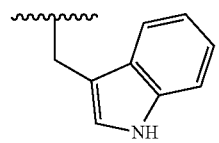

In another embodiment, the disclosure provides a method of preparing isopropyl (S)-2-((S)-2-acetamido-3-(1H-indol-3-yl)propanamido)-6-diazo-5-oxohexanoate in a yield of about 50% or more, the method comprising reacting isopropyl (S)-2-amino-6-diazo-5-oxohexanoate with acetyl-L-tryptophan in the presence of ethyl cyano(hydroxyimino)acetate and N,N'-dicyclohexylcarbodiimide. In another embodiment, yield is about 55% or more. In another embodiment, yield is about 60% or more. In another embodiment, yield is about 65% or more. In another embodiment, yield is about 70% or more. In another embodiment, yield is about 75% or more. In another embodiment, yield is about 80% or more. In another embodiment, yield is about 85% or more. In another embodiment, yield is about 90% or more. In another embodiment, yield is about 95% or more.

In another embodiment, the disclosure provides a method of preparing isopropyl (S)-2-((S)-2-acetamido-3-(1H-indol-3-yl)propanamido)-6-diazo-5-oxohexanoate in about 95% chemical purity or more, the method comprising reacting isopropyl (S)-2-amino-6-diazo-5-oxohexanoate with acetyl-L-tryptophan in the presence of ethyl cyano(hydroxyimino)acetate and N,N'-dicyclohexylcarbodiimide. In another embodiment, the chemical purity is about 96% or more. In another embodiment, the chemical purity is about 97% or more. In another embodiment, the chemical purity is about 98% or more. In another embodiment, the chemical purity is about 99% or more.

In another embodiment, the disclosure provides a method of preparing isopropyl (S)-2-((S)-2-acetamido-3-(1H-indol-3-yl)propanamido)-6-diazo-5-oxohexanoate in about 95% ee or more, the method comprising reacting isopropyl (S)-2-amino-6-diazo-5-oxohexanoate with acetyl-L-tryptophan in the presence of ethyl cyano(hydroxyimino)acetate and N,N'-dicyclohexylcarbodiimide. In another embodiment, the ee is about 96% or more. In another embodiment, the ee is about 97% or more. In another embodiment, the ee is about 98% or more. In another embodiment, the ee is about 99% or more.

In another embodiment, the disclosure provides a method of preparing a compound of Formula I from L-pyroglutamic acid according to the following scheme:

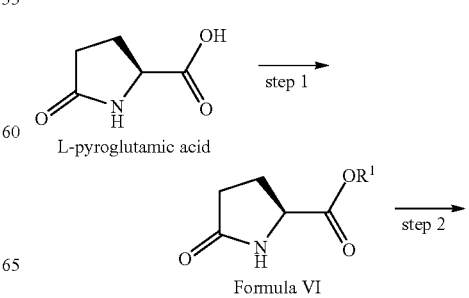

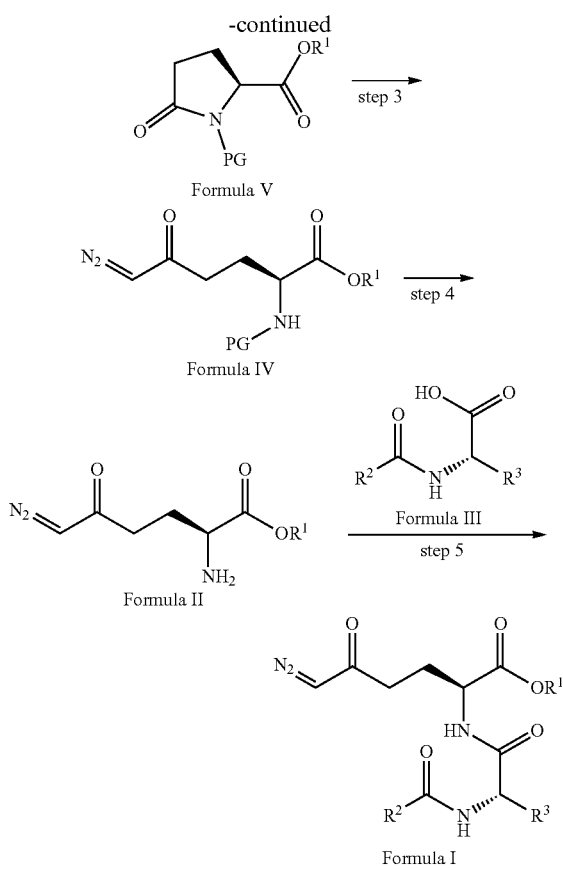

wherein $R^1$ is $C_1$-$C_4$ alkyl; $R^2$ is $C_1$-$C_4$ alkyl; $R^3$ is selected from the group consisting of $C_1$-$C_6$ alkyl, (aryl)alkyl, and (heteroaryl)alkyl; and PG is a protecting group, and the reagents and conditions of steps 1-5 are described above in connection with the preparation of Formulae I, II, IV, V, and VI.

Figure 6:
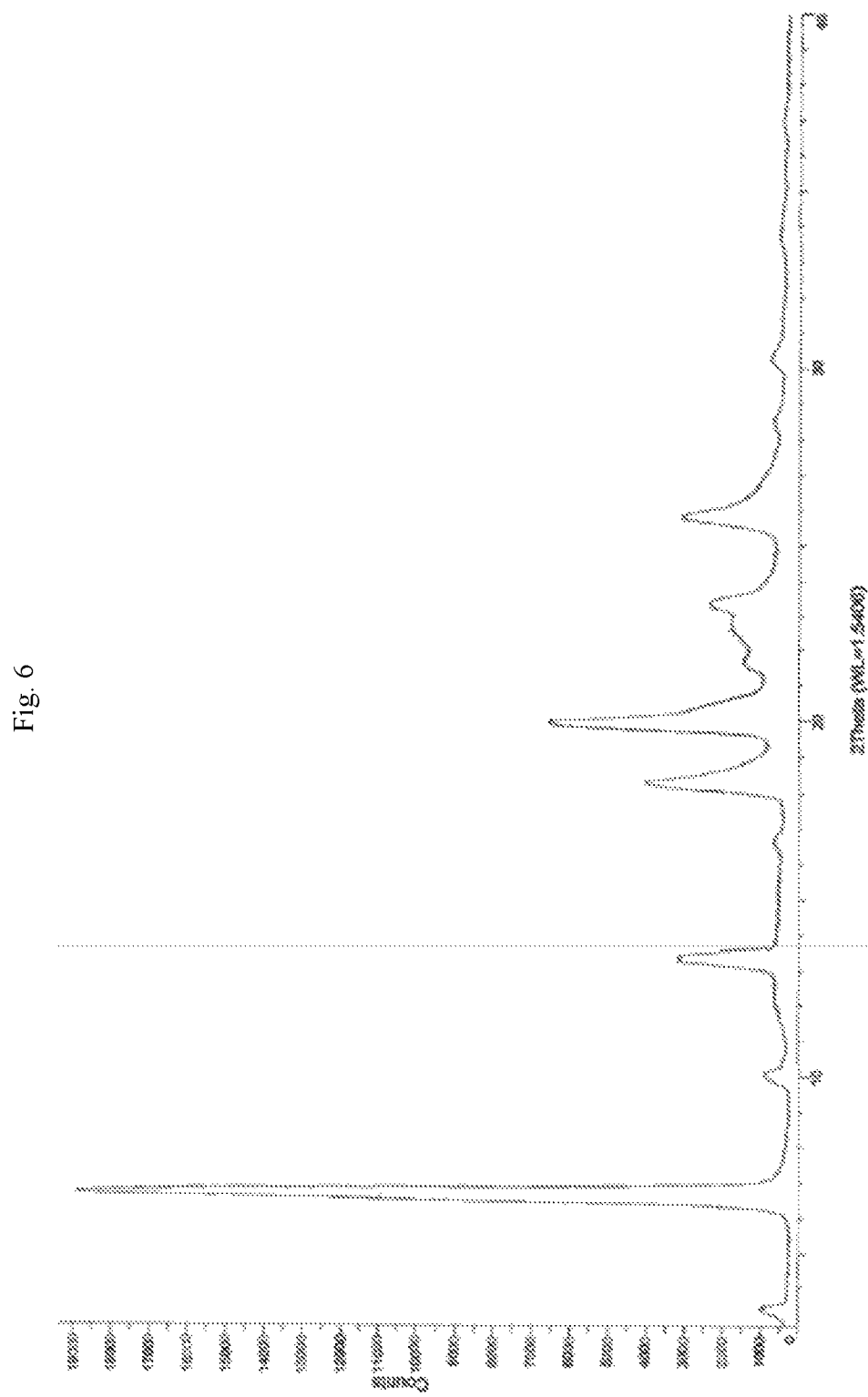
FIG. 6 is a XRPD diffractogram of Compound 5 ((isopropyl (S)-2-((S)-2-acetamido-3-(1H-indol-3-yl)propanamido)-6-diazo-5-oxohexanoate).

In another embodiment, the disclosure provides a crystalline form of (S)-2-((S)-2-acetamido-3-(1H-indol-3-yl)propanamido)-6-diazo-5-oxohexanoate characterized as having powder x-ray diffraction (PXRD) peaks at 6.6, 13.3, 18.3, 20.0, 23.4, and 25.8 degrees 2Θ. In another embodiment, the disclosure provides a crystalline form of (S)-2-((S)-2-acetamido-3-(1H-indol-3-yl)propanamido)-6-diazo-5-oxohexanoate characterized as having a PXRD pattern that is essentially the same as FIG. 6. In another embodiment, the disclosure provides a crystalline form of (S)-2-((S)-2-acetamido-3-(1H-indol-3-yl)propanamido)-6-diazo-5-oxohexanoate characterized as having any 3, 4, 5, 6, or more of the PXRD peaks and/or relative intensities listed in Table 7.

Definitions

The term "halo" as used herein by itself or as part of another group refers to —Cl, —F, —Br, or —I.

The term "nitro" as used herein by itself or as part of another group refers to —NO$_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to six carbon atoms, i.e., a $C_1$-$C_6$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl, i.e., methyl, ethyl, propyl, isopropyl, butyl, isobutyl, or tert-butyl.

The term "alkoxy" as used herein by itself or as part of another group refers to an alkyl group attached to a terminal oxygen atom. In one embodiment, the alkyl is a $C_1$-$C_4$ alkyl group. Non-limiting exemplary alkoxy groups include methoxy, ethoxy, and tert-butoxy.

The term "(aryl)alkyl" as used herein by itself or as part of another group refers to an alkyl substituted with one optionally substituted aryl group. In one embodiment, the aryl is an optionally substituted phenyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl and 4-OH-benzyl.

The term "aryl" as used herein by itself or as part of another group refers to phenyl (abbreviated as "Ph") or naphthyl groups. In another embodiment, the aryl group is phenyl.

The term "optionally substituted aryl" as used herein by itself or as part of another group refers to a phenyl or naphthyl groups that is either unsubstituted or substituted with one to five substituents, wherein the substituents are each independently halo, nitro, cyano, hydroxy, —NH$_2$, $C_1$-$C_4$ alkyl, or $C_1$-$C_4$ alkoxy. Non-limiting exemplary optionally substituted aryl groups include 4-fluorophenyl and 4-OH-phenyl, The term "(heteroaryl)alkyl" as used herein by itself or as part of another group refers to an alkyl substituted with one optionally substituted 5- to 14-membered heteroaryl group. In one embodiment, the alkyl group is substituted with one optionally substituted 5- to 9-membered heteroaryl group. In another embodiment, the alkyl group is a $C_1$-$C_4$ alkyl. In another embodiment, the alkyl group is a $C_1$ or $C_2$ alkyl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 9-membered heteroaryl. Non-limiting exemplary heteroaryl groups include thienyl, pyrrolyl, imidazolyl, pyrazolyl, indolyl, and indazolyl.

The term "optionally substituted heteroaryl" as used herein by itself or as part of another group refers to a heteroaryl that is either unsubstituted or substituted with one to four substituents, wherein the substituents are independently halo, nitro, cyano, hydroxy, —NH$_2$, $C_1$-$C_4$ alkyl, or $C_1$-$C_4$ alkoxy.

The term "protecting group" as used herein refers to group that blocks, i.e., protects, the amine functionality while reactions are carried out on other functional groups or parts of the molecule. Those skilled in the art will be familiar with the selection, attachment, and cleavage of protecting groups and will appreciate that different protective groups are known in the art, the suitability of one protective group or another being dependent on the particular the synthetic scheme planned. Treatises on the subject are available for consultation, such as Wuts, "Greene's Protective Groups in Organic Synthesis", 5th Ed., J. Wiley & Sons, Inc., NY, 2014. Suitable protecting groups include carbobenzyloxy (Cbz), tert-butyloxycarbonyl (BOC), 9-fluorenylmethyloxycarbonyl (FMOC) and benzyl (Bn) groups.

The term "base" as used herein refers to an organic proton acceptor. Non-limiting bases include non-nucleophilic tertiary amines, e.g., NEt₃ iPr₂NEt, N-methylmorpholine, and nitrogen-containing heteroaromatic groups such as pyridine, and derivatives of pyrindine, e.g., 2,4,6-collidine.

The term "isopropyl (S)-2-((S)-2-acetamido-3-(1H-indol-3-yl)propanamido)-6-diazo-5-oxohexanoate" as used herein refers to a compound having the following structure:

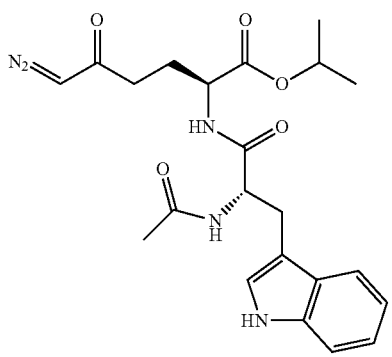

The term "ethyl (S)-2-((S)-2-acetamido-3-(1H-indol-3-yl)propanamido)-6-diazo-5-oxohexanoate" as used herein refers to a compound having the following structure:

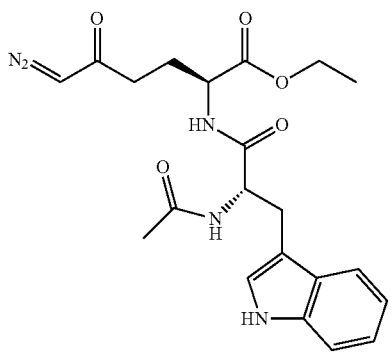

The term "isopropyl (S)-5-(diazomethyl)-3,4-dihydro-2H-pyrrole-2-carboxylate" as used herein refers to a compound having the following structure:

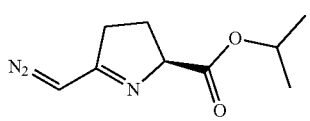

The term "ethyl (S)-5-(diazomethyl)-3,4-dihydro-2H-pyrrole-2-carboxylate" as used herein refers to a compound having the following structure:

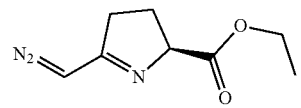

The term "acetyl-L-tryptophan" as used herein refers to a compound having the following structure:

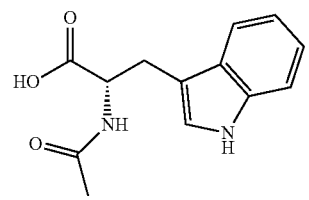

The term "isopropyl (S)-2-amino-6-diazo-5-oxohexanoate" as used herein refers to a compound having the following structure:

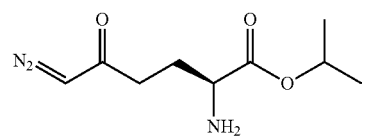

The term "stereomutation" as used herein refers to a change of configuration at a chiral center brought about by chemical means.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "a" and "an" refer to one or more than one.

The term "about," as used herein, includes the recited number ±10%. Thus, "about 10" means 9 to 11.

As used herein, the term "essentially the same" with reference to PXRD peak positions and/or relative intensities means that peak position and intensity variability are taken into account when comparing PXRD diffractograms that show inter-apparatus variability of more than 0.2°. Relative peak intensities can show inter-apparatus variability due to degree of crystallinity, orientation, prepared sample surface, and other factors known to those skilled in the art, and should be taken as qualitative measures only.

The following definitions may be used:

| | |
|---|---|
| eq. | Equivalent(s) |
| Kg | Kilogram(s) |
| g | gram(s) |
| h | Hour(s) |
| HPLC | high-performance liquid chromatography |
| LCMS | liquid chromatography mass spectrometry |
| mL | milliliter |
| Temp. | temperature |
| THF | tetrahydrofuran |
| DCM | dichloromethane |
| GC | Gas Chromatography |
| DMF | N,N-dimethylformamide |
| NMP | 1-methylpyrrolidin-2-one |
| atm. | Standard atmospheric pressure |
| TEA | triethylamine |
| V | volume |
| ACN | acetonitrile |
| SM | Starting Material |
| MTBE | 2-methoxy-2-methylpropane |
| IPA | propan-2-ol |
| EtOAc | ethyl acetate |
| DMSO | Dimethyl sulfoxide |

Example 1

Synthesis of isopropyl (S)-5-oxopyrrolidine-2-carboxylate (Compound 1)

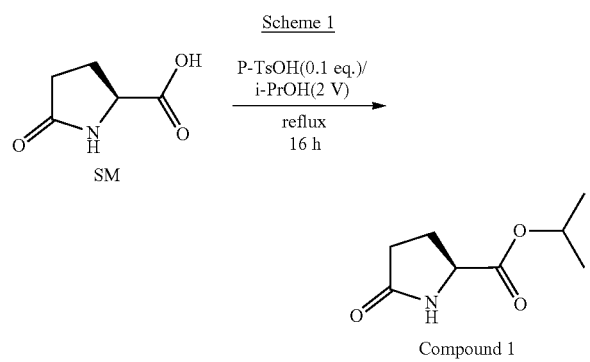

Scheme 1

Table 1 provides the starting materials and results of the chemical reaction described in Scheme 1. All reactions were carried out using 0.1 eq. p-TsOH in i-PrOH, and all reactions were heated to reflux for approximately 16 h.

TABLE 1

| Entry | SM | Result |
|---|---|---|
| 1 | 150 g (1.0 eq.) i-PrOH (2 V) | 138 g off-white solid, yield: 69% |
| 2 | 95 g (1.0 eq.) Racemate i-PrOH (2 V) | 88 g off-white solid (racemate), yield: 69% |
| 3 | 684 g (1.0 eq.) i-PrOH (2 V) | 609 g off-white solid, yield: 67%, ee >99% |
| 4 | 1.0 kg (1.0 eq.) | 1.02 Kg white solid obtained with 99.8% HPLC purity and 100% ee, yield: 76.9%. |

Process Description for Entry 3 of Table 1
1. Charged propan-2-ol (1.37 L, 2 V) into a 5 L reactor.
2. Charged (S)-5-oxopyrrolidine-2-carboxylic acid (684 g, 1.0 eq.) into the reactor with stirring.
3. Charged 4-methylbenzenesulfonic acid (91.2 g, 0.1 eq.) into the reactor.
4. Heated to reflux.
5. Stirred overnight at reflux.
6. Cooled to below 30° C.
7. Concentrated under vacuum.
8. Dissolved the residue in DCM (10 V) and washed with sat. NaHCO₃ (3 V), water (1.5 V), and brine (1.5 V).
9. Combined the aqueous phases and extracted with DCM (5 V) then washed the extraction with water (1 V) and brine (1 V).
10. Combined the organic phases in step 8 and step 9 and concentrated under vacuum.
11. This resulted in 609 g of Compound 1 as an off-white solid (yield 67%; ee>99%) that could be used directly to the next step without any further purification.

Process Description for Entry 4 of Table 1
1. Charged propan-2-ol (10 L, 10 V) into a 20 L reactor under N₂ protection.
2. Charged (S)-5-oxopyrrolidine-2-carboxylic acid (1 Kg, 1.0 eq.) into the reactor with stirring.
3. Charged 4-methylbenzenesulfonic acid (133.3 g, 0.1 eq.) into the reactor.
4. Heated to reflux and stirred overnight at reflux.
5. Cooled to below 30° C. and concentrated under vacuum to less than 1 V left.
6. Dissolved the residue with DCM (10 V) and washed with NaHCO₃ (sat., 3 V), water (1.5 V) and brine (1.5 V).
7. Combined the aqueous phases and extracted with DCM (5 V) and then washed the extraction with water (1 V) and brine (1 V).
8. Combined the organic phases and concentrated under vacuum to ~1 V left.
9. Charged n-heptane (3 V) into the residue with stirring.
10. Cooled to below 10° C. and stirred for at least 1 h at 0-10° C.
11. Filtration and washed the filter cake with n-heptane (0.5 V).
12. This resulted 580 g white solid after drying with high purity.
13. Concentrated the filtrate under vacuum.
14 Dissolved the residue with DCM (10 V) and washed with NaHCO₃ (sat., 3 V), water (1.5 V), and brine (1.5 V).
15. Combined the aqueous phases and extracted with DCM (5 V) and then washed the extraction with water (1 V) and brine (1 V).
16. Combined the organic phases and concentrated under vacuum to ~1 V left.

Figure 4:
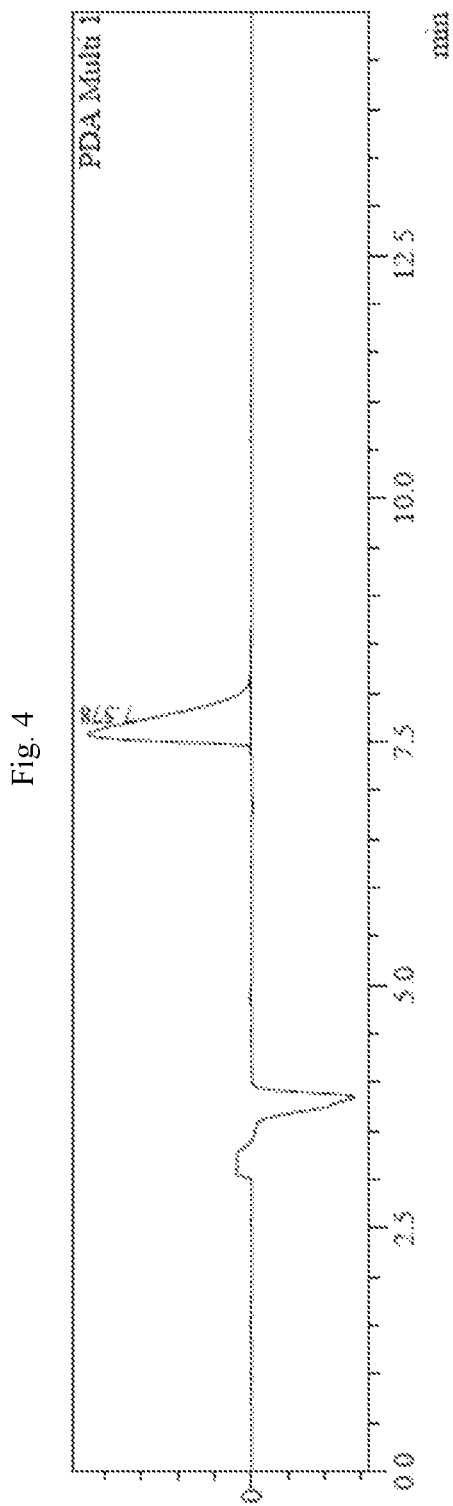
FIG. 4 is a chiral HPLC chromatogram showing the enantiomeric excess (ee) of Compound 1 obtained by the synthetic method described in EXAMPLE 1, Table 1, Entry 4.
Figure 5:
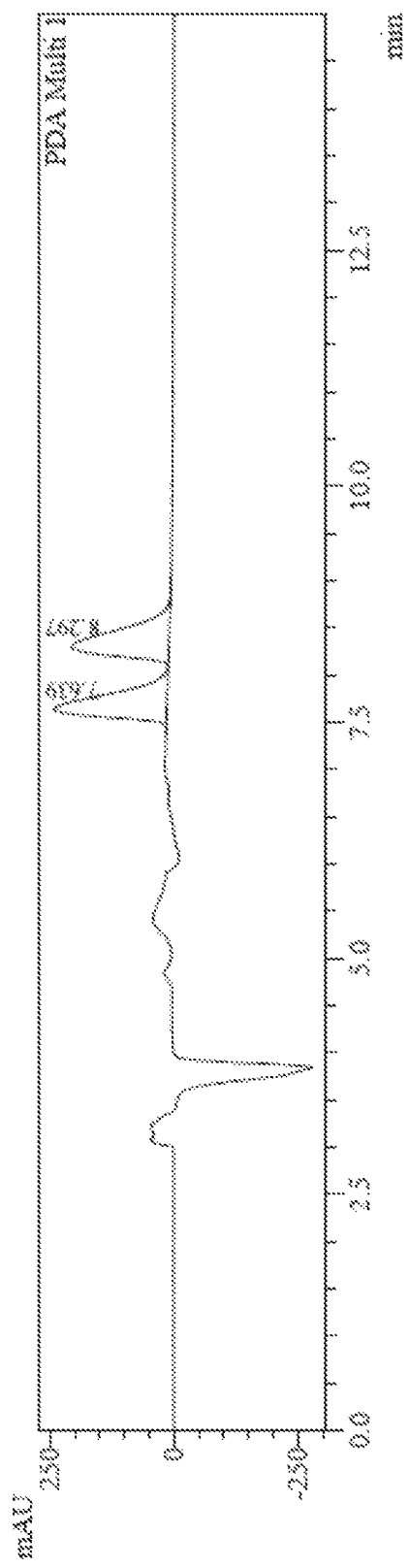
FIG. 5 is a chiral HPLC chromatogram showing the chiral resolution of racemic Compound 1.

17. Charged n-heptane (3 V) into the residue with stirring.
18. Cooled to below 10° C. and stirred for at least 1 h at 0-10° C.
19. Filtered and washed the filter cake with n-heptane (0.5 V).
20 This resulted another 440 g white solid after drying with high purity.
21. Total 1.02 Kg white solid obtained with 99.8% HPLC purity and 100% ee. See FIG. 4 and FIG. 5.

Example 2

Synthesis of 1-((9H-fluoren-9-yl)methyl) 2-isopropyl (S)-5-oxopyrrolidine-1,2-dicarboxylate (Compound 2)

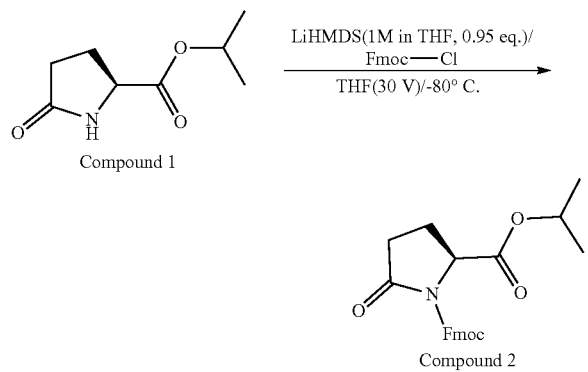

Scheme 2

Compound 1

Compound 2

Table 2 provides the starting materials, reaction times, and results of the chemical reaction described in Scheme 2. All reactions were carried out using 0.95 eq. of LiHMDS (1 M in THF) at −80±5° C. in THF. No Compound 1 remained after the reaction time indicated.

| Entry | Starting Materials | | Reaction Time (h) | Result |
|---|---|---|---|---|
| | Compound 1 | Fmoc—Cl | | |
| 1 | 2.0 g (1.0 eq.) THF (30 V) | 5.0 eq. | 1.0 | 2.8 g of Compound 2 as a white solid with ~98% purity was obtained from 10 g of crude product by column chromatography, |
| 2 | 20.0 g (1.0 eq.) THF (30 V) | 5.0 eq. | 0.5 | 190 g of white solid with~95% purity was obtained by slurry and 60 g of white solid was obtained with >95% purity from the mother liquor, ee >99%. |
| 3 | 138.0 g (1.0 eq.) THF (30 V) | 2.0 eq. | 0.5 | |
| 4 | 80.0 g (1.0 eq.) Racemate THF (30 V) | 2.0 eq. | 0.5 | 143 g white solid was obtained with 97.9% HPLC purity (racemate), Yield: 77% |
| 5 | 280.0 g (1.0 eq.) THF (30 V) | 2.0 eq. | 0.5 | 536 g white solid was obtained with 97.9% HPLC purity, yield: 83% |
| 6 | 500.0 g (1.0 eq.) THF (15 V) | 1.05 eq. | 0.5 | HPLC purity 99.2%; chiral HPLC: 100% |

Process Description of Entry 5 of Table 2
1. Charged THF (4.2 L, 15 V) into a 10 L reactor under N2.
2. Charged Compound 1 (280 g, 1.0 eq.) with stirring into the reactor, and cooled to −80° C.
3. Charged dropwise a solution of LiHMDS (1 M in THF, 1.55 L, 0.95 eq.) at −80±5° C. and stirred for ~30 min at −80±5° C. (Solution 1).
4. Charged THF (4.2 L, 15 V) and Fmoc-Cl (816.2 g, 2.0 eq.) into another 20 L reactor under $N_2$ and cooled to −80° C.
5. Transferred Solution 1 into the 20 L reactor of Step 4 with stirring at −80±5° C.
6. Stirred for 30 min and then sampled for Compound 1. No Compound 1 remained.
7. Quenched the reaction with sat. $NH_4Cl$ until the pH was adjusted to 6~7 below −70° C.
8. Warmed to −10~0° C.
9. Phase separated and collected the organic phase.
10. Washed the organic phase with half sat. brine (3 V) and sat. brine (3 V).
11. Concentrated the organic phase and switched with MTBE (5 V×2) until less than 6 V left.
12. Charged MTBE (3 V) into the reactor and stirred for 20 min.
13. Charged n-heptane (5 V) into the mixture and then stirred overnight at room temperature.
14. Filtered and collected the solid.
15. Re-slurried the solid with DCM (2.8 L, 10 V) for 30 min and then filtered the solid.
16. Concentrated the filtrate and switched with MTBE (3 V×2) until less than 3 V left.
17. Charged MTBE (1 V) and n-heptane (1.5 V) into the residue and stirred overnight.
18. Filtered and collected the solid.
19. This resulted in 536 g of Compound 2 as a white solid with 97.9% HPLC purity (yield: 83%).

Process Description of Entry 5 of Table 2
1. Charged THF (5 L, 10 V) into a 20 L reactor under $N_2$ protection.
2. Charged Compound 1 (500 g, 1.0 eq.) into the reactor with stirring.
3. Cooled to below −80° C.
4. Charged dropwise a solution of LiHMDS (1 M in THF, 2.75 L, 0.95 eq.) into the reactor while maintaining the temperature at −80±5° C.
5. Stirred for ~30 min at −80±5° C. (Solution 1).
6. Charged dropwise a solution of Fmoc-Cl (795 g, 1.05 eq.) in THF (5 V) into solution 1 with stirring at −80±5° C.
7. Stirred for 30 min at −80±5° C.
8. Sampled for IPC (Compound 1 left).
9. Charged water (7.5 V) and AcOH (2.0 eq.) into another 20 L reactor.
10. Cooled to 0° C. (Solution 2).
11. Transferred Solution 1 into the above Solution 2 with stirring via $N_2$ press at 0±5° C.
12. Warmed to 10~15° C.
13. Phase separated and collected the above organic phase.
14. Washed the organic phase with half sat. brine (5 V×2).
15. The same reaction was repeated at the same scale and combined the organics together.
16. Concentrated the combined organic phase under vacuum until the residue no more than 5 V left.
17. Switched with IPA (5 V×2) until the residue less than 8 V left.
18. Stirred for 2-3 h at 25~30° C.

19. Filtered, collected the solid, and dried to give Compound 2 in high chemical purity and 100% chiral purity.

Example 3

Synthesis of isopropyl (S)-2-((((9H-fluoren-9-yl)methoxy)carbonyl)amino)-6-diazo-5-oxohexanoate (Compound 3)

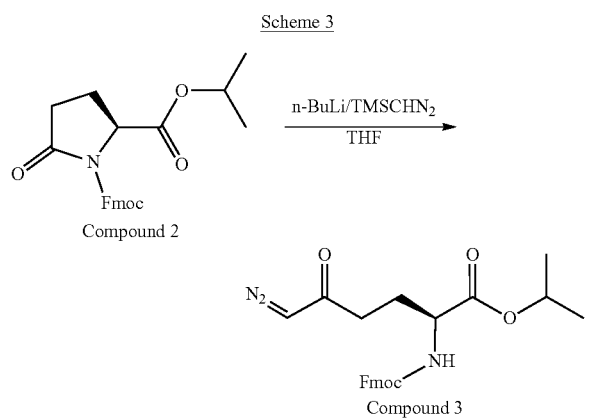

Scheme 3

Table 3 provides the starting materials, reaction temperatures, reaction times, percentages of Compound 2 remaining after the indicated reaction time, and results of the chemical reaction described in Scheme 3. All reactions were carried out in THF (30 V).

Process Description for Entry 6 of Table 3
1. Charged THF (1.5 L, 15 V) into a 5 L reactor under $N_2$.
2. Charged TMSCHN$_2$ (2 M in n-hexane, 152.5 mL, 1.2 eq.) into the reactor with stirring.
3. Cooled to below −80° C.
4. Charged dropwise n-BuLi (2.5 M in n-hexane, 125 mL, 1.23 eq.) into the reactor while maintaining the temperature at −85±5° C.
5. Stirred for ~30 min at −85±5° C. (Solution 1).
6. Charged THF (2 L, 20 V) and Compound 2 (100 g, 1.0 eq.) into another 5 L reactor under $N_2$.
7. Cooled to ~−90° C. with stirring.
8. Transferred Solution 1 into the reactor of Step 7 with stirring while maintaining the temperature below −85° C.
9. Stirred for 15 min at −85±5° C.
10. Sampled for Compound 2. Approximately 2.8% of Compound 2 remained.
11. Quenched the reaction with sat. NH$_4$Cl (1 L, 10 V) below −80° C.
12. Warmed to 0° C.
13. Phase separated and collected the organic phase.
14. Washed the organic phase with half sat. brine (5 V) and sat. brine (5 V).
15. Concentrated the organic phase under vacuum and switched with MTBE (5 V×3) until the residue less than 3 V left.
16. Charged MTBE (5 V) into the residue and stirred overnight at room temperature.
17. Filtered and washed the solid with MTBE (1.5 V).
18. Collected the solid and dried.
19. This resulted in 88.5 g of Compound 3 light yellow solid with ~85% HPLC purity which could be used to the next step directly without any purification.

Process Description for Entry 7 of Table 3
1. Charged THF (500 mL, 10 V) into a 2 L reactor under $N_2$ protection.
2. Charged Compound 2 (50 g, 1.0 eq.) into the reactor with stirring.
3. Cooled to below −60° C.
4. Charged TMSCHN$_2$ (2 M in hexane, 76.3 mL, 1.20 eq.) into reactor at below −60° C.
5. Cooled to −90±10° C.
6. Charged dropwise n-BuLi (2.5 M in n-hexane, 1.23 eq.) into reactor at −90±10° C. (over ~1.7 h).
7. Stirred for 30~60 min at −90±10° C.
8. Sampled for IPC (14.5% Compound 2 left, prolong time no progress).
9. Charged dropwise additional n-BuLi (2.5 M in n-hexane, 0.18 eq.) into reactor at −90±10° C.
10. Stirred for 30~60 min at −90±10° C.
11. Sampled for IPC (7.4% Compound 2 left, prolong time no progress).
12. Charged dropwise additional n-BuLi (2.5 M in n-hexane, 0.09 eq.) into reactor at −90±10° C.
13. Stirred for 30~60 min at −90±10° C.
14. Sampled for IPC (6.8% Compound 2 left).
15. Charged dropwise AcOH (1.5 eq., 1.0 eq. of n-BuLi) into reactor at below −80° C. (over ~0.5 h).
16. Warmed to 0° C. (over ~1 h).
17. Charged dropwise 20% aq. NH$_4$Cl solution (5.0 w/w) into reactor at 0-5° C. (over ~1 h).
18. Warmed to 25±5° C.
19. Stirred for 0.5 h at 25±5° C.
20. Sampled for IPC (0.3% intermediate left).
21. Phase separated and washed the organic phase with half sat. brine (5 V×2).
22. Concentrated under vacuum below 35° C. to 2.5~3.0 V left.
23. Charged dropwise n-heptane (20 V) slowly to the residue at 20±5° C.
24. Stirred overnight at 20±5° C.
25. Filtration and washed the solid with n-heptane (5 V).
26. Sampled the filter cake for HPLC analysis (HPLC purity: 80.2%.
27. Dissolved the above filter cake in DCM (2 V).
28. Charged dropwise n-heptane (18 V) slowly to the residue at 20±5° C.
29. Filtration and washed the solid with n-heptane (4 V).
30. Sampled the filter cake for HPLC analysis (HPLC purity: 86.6%).
31. After further purification (process as step 27 to step 30), obtained the solid with 90.6% HPLC purity.
32. Collected 29.6 g of brown solid after drying.

Example 4

Synthesis of isopropyl (S)-2-amino-6-diazo-5-oxohexanoate (Compound 4)

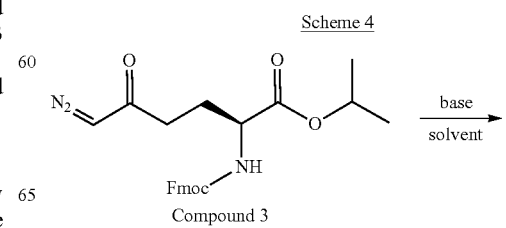

Scheme 4

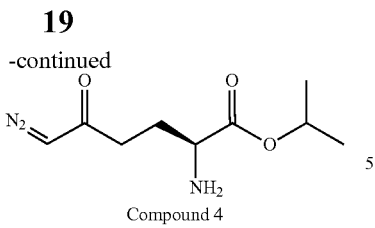

Compound 4

Table 4 provides the starting materials, solvents, reaction temperatures, reaction times, percentages of Compound 3 remaining after the indicated reaction time, and results of the chemical reaction described in Scheme 4. All reactions were carried out in THE (30 V).

The following by by-products of the reaction in Scheme 4 could be detected by MS:

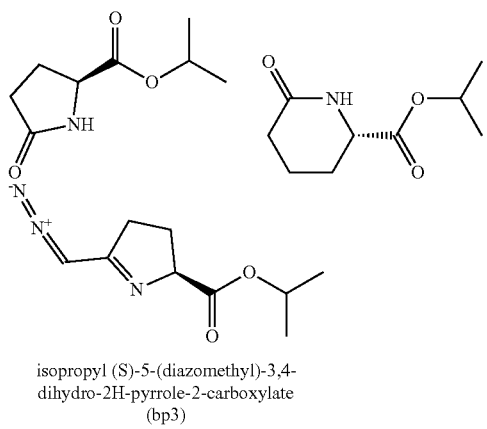

isopropyl (S)-5-(diazomethyl)-3,4-dihydro-2H-pyrrole-2-carboxylate
(bp3)

This reaction worked quickly with more amine, such as piperidine, morpholine, cyclohexanamine.

Compound 4 was chemically unstable and thus was difficult to isolate the from reaction mixture. As Entry 10 shows, isopropyl (S)-5-(diazomethyl)-3,4-dihydro-2H-pyrrole-2-carboxylate was detected by HPLC. But after purification by column chromatography for the second time only isopropyl (S)-5-(diazomethyl)-3,4-dihydro-2H-pyrrole-2-carboxylate was detected on HPLC.

The reaction mixture comprising Compound 4 had to be used directly in the last step without any work-up to synthesize the final product because it could not be isolated and effectively purified.

Example 5

Synthesis of Isopropyl (S)-2-((S)-2-acetamido-3-(1H-indol-3-yl)propanamido)-6-diazo-5-oxohexanoate (Compound 5) using OxymaPure®

Scheme 5

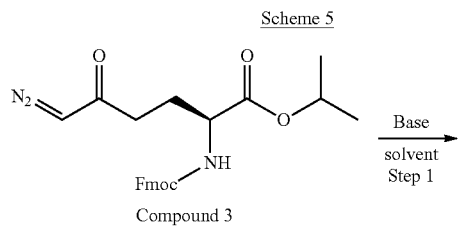

Compound 3

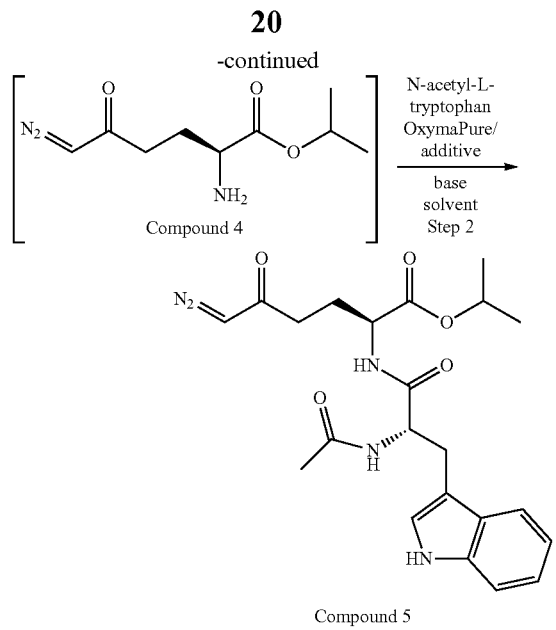

Compound 5

Tables 5A-5F provide the starting materials, solvents, reaction temperatures, reaction times, percentages of Compound 3 remaining after the indicated reaction time, and results of the chemical reaction described in Scheme 5.

Process Description for Entry 3 of Table 5C
1. Charged DCM (1.04 L, 8 V) into a 2 L reactor under $N_2$.
2. Charged Compound 3 (130 g, 1.0 eq.) into the above reactor with stirring.
3. Cooled to below 10° C. and then charged piperidine (64.13 g, 2.5 eq.) into the reactor.
4. Stirred for 4 h at 10±5° C.
5. Sampled and determined that ~4% Compound 3 remained (Solution 1).
6. Charged DMF (2.6 L, 20 V) into another 5 L reactor under $N_2$.
7. Charged N-acetyl-L-tryptophan (258.6 g, 3.5 eq.) into the 5 L reactor of step 6 with stirring.
8. Charged DIC (132.5 g, 3.5 eq.), OxymaPure® (149.2 g, 3.5 eq.), and 2,4,6-collidine (166 g, 4.55 eq.) into the reactor.
9. Transferred Solution 1 into the above 5 L reactor with stirring via $N_2$ pressure below 25° C.
10. Stirred for 2 h at 20±5° C.
11. Sampled for IPC analysis—SM (N-acetyl-L-tryptophan): P=42.4%:48.7%).
12. Charged the reaction mixture into water (7.8 L, 60 V) slowly with stirring.
13. Charged DCM (2.6 L, 20 V) into the mixture and stirred for 15 min.
14. Phase separated and extracted the aqueous phase with DCM (3.9 L×2, 30 V×2).
15. Combined the organic phases and washed with 1 M $KHSO_4$ solution (1.3 L, 10 V).
16. Concentrated the organic phase under vacuum.
17. Charged MTBE (2.6 L, 20 V) into the residue and stirred for more than 2 h at room temperature.
18. Filtered out the solid and washed with MTBE (6 V).
19. Collected the filtrate and washed with water (8 V×2) and brine (8 V×1). HPLC showed that the product was washed out.
20. Extracted the aqueous phase with MTBE (15 V×4) and washed the organic phase with water (5 V×1). HPLC showed there was still product left in the aqueous phase.

21. Extracted the above aqueous phase again with DCM (10 V×2).

22. Washed the extraction with water (6 V×3).

23. Combined the above organics in and concentrated under vacuum. This resulted 756 g dark brown oil that was purified by column chromatography (DCM:MeOH=80:1~20:1) and concentrated the eluent under vacuum to ~500 mL left.

24. Switched with EtOAc (500 ml×2) until the residue was ~200 mL left.

25. Stirred for 0.5~1 h at 15~20° C.

26. Filtered and washed the solid with EtOAc.

27. Collected the solid and dried.

Figure 2:
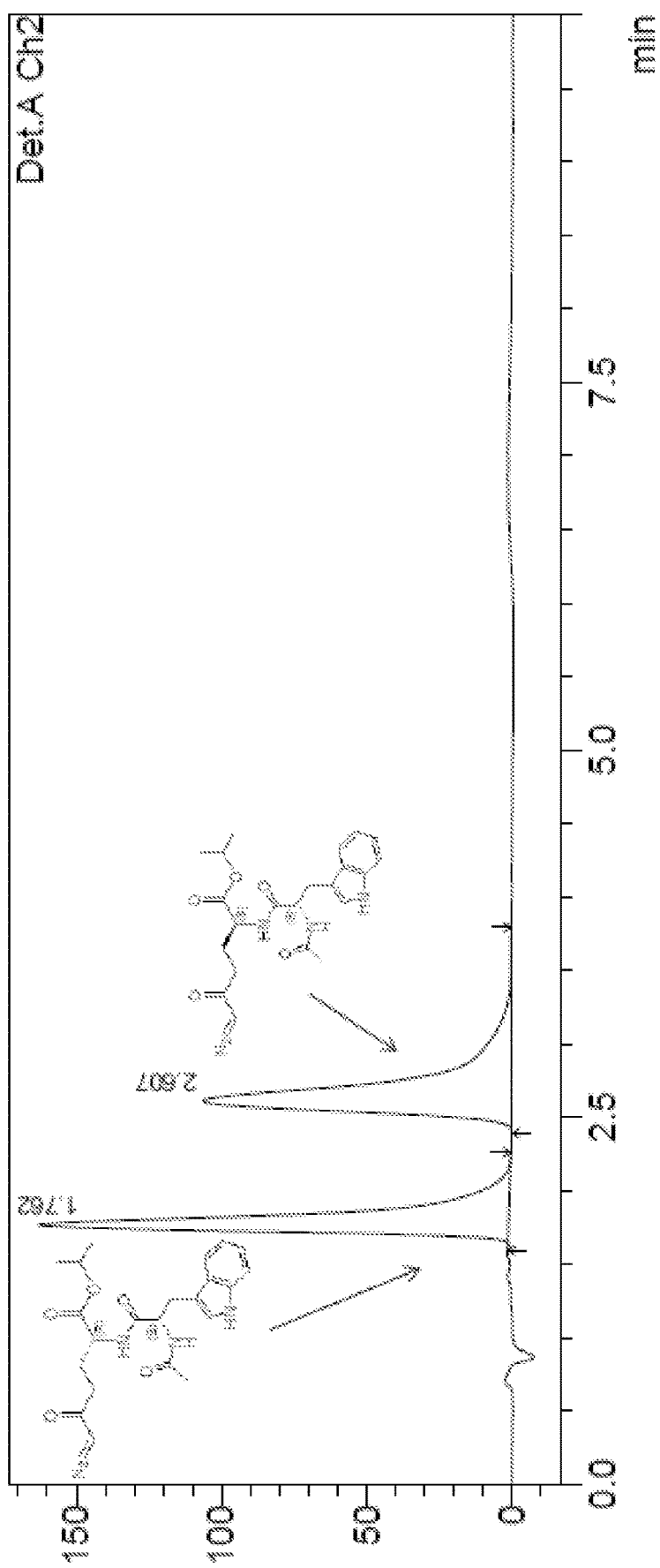
FIG. 2 is a chiral HPLC chromatogram showing the chiral resolution of a sample containing isopropyl (R)-2-((S)-2-acetamido-3-(1H-indol-3-yl)propanamido)-6-diazo-5-oxohexanoate and isopropyl (S)-2-((S)-2-acetamido-3-(1H-indol-3-yl)propanamido)-6-diazo-5-oxohexanoate.
Figure 3:
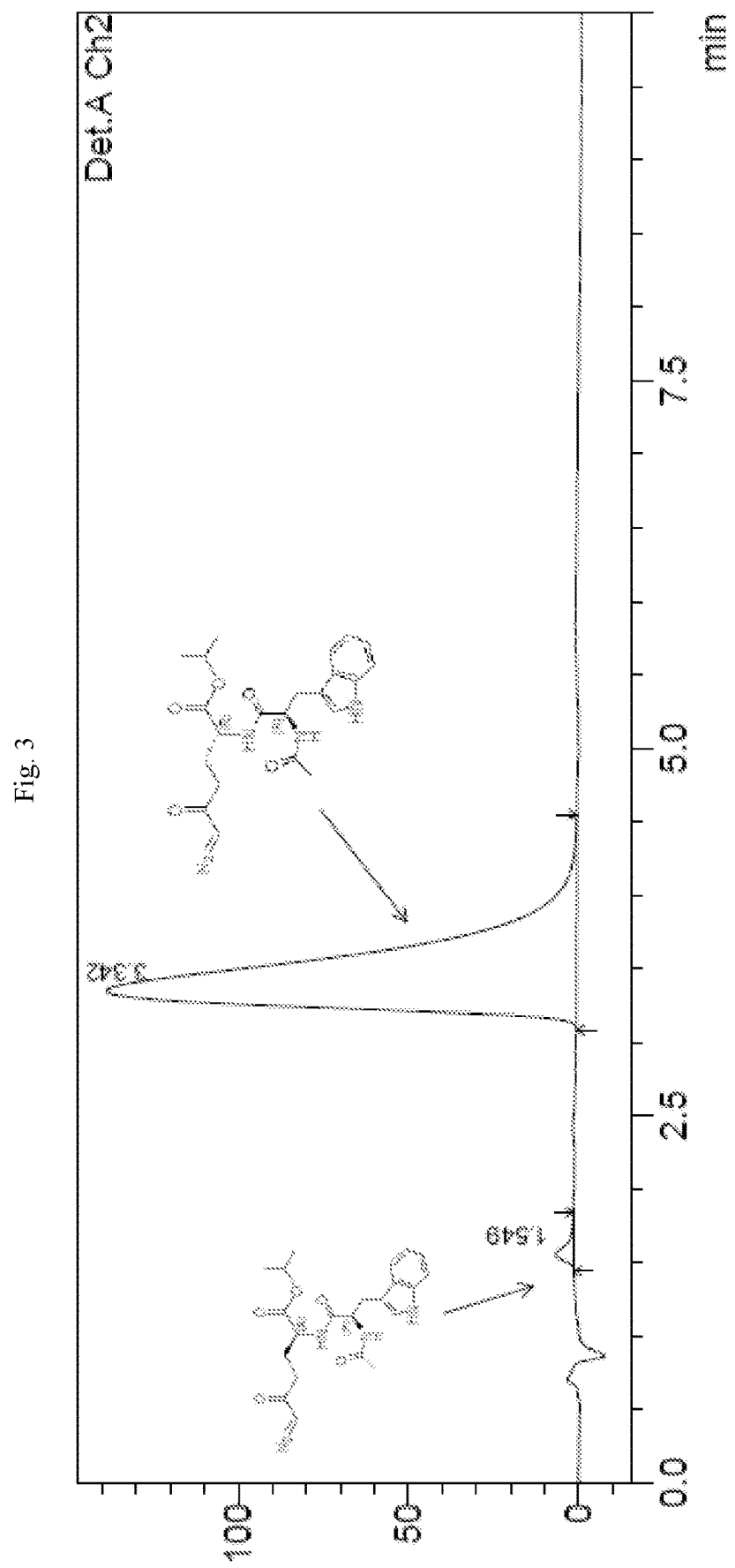
FIG. 3 is a chiral HPLC chromatogram showing the enantiomeric excess (ee) of Compound 5 (isopropyl (S)-2-((S)-2-acetamido-3-(1H-indol-3-yl)propanamido)-6-diazo-5-oxohexanoate) obtained by the synthetic method described in EXAMPLE 5.

28. This resulted in 65 g of Compound 5 as yellow solid in 99.1% chemical purity and 98.9% ee. See FIGS. 1-3. Compound 5 was not stable under acidic conditions. The following analytic HPLC conditions were used to determine chemical purity:

| Column | Poroshell HPH-C18 4.6 × 50 mm, 2.7 μm |
| --- | --- |
| Mobile phase A | 0.1% NH$_4$OH in Water |
| Mobile phase B | ACN |
| Column temperature | 40° C. |
| Detector | 220 nm |
| Flow rate | 1.0 mL/min |
| Run time | 8.1 minutes |
| Post time | 1.5 minutes |
| Diluent | ACN |

| Time (min) | 0.0 | 4.5 | 6 | 8 | 8.1 |
| --- | --- | --- | --- | --- | --- |
| % Mobile Phase A | 90 | 50 | 0 | 0 | 90 |
| % Mobile Phase B | 10 | 50 | 100 | 100 | 10 |

The following chiral HPLC conditions were used to determine ee:

| Column | CHIRALPAK IA-3 4.6 × 50 mm, 3 μm |
| --- | --- |
| Mobile phase A | 0.1% DEA in Hex |
| Mobile phase B | IPA |
| Column temperature | 25° C. |
| Detector | 220 nm |
| Flow rate | 1.0 mL/min |
| Run time | 8 minutes |
| Gradient | Mobile phase A:Mobile phase B = 80:20 |
| Diluent | ETOH |

Process Description for Entry 4 of Table 5D

1. Charged diethyl amine (17.5 mL, 3.5 V) into reactor under N$_2$ atmosphere.

2. Cooled to below 10° C.

3. Charged Compound 3 (5.0 g, 1.0 eq.) into the reactor with stirring.

4. Stirred for 1 hour at 5±5° C.

5. Sampled for IPC analysis (HPLC showed no Compound 3 left).

6. Concentrated the reaction mixture at room temperature under vacuum until the residue was no more than 2 V left.

7. Switched with DCM (4 V) three times until the residue was no more than 2 V left.

8. Diluted the residue with DCM (5 V) to obtain Solution 1.

9. Charged DCM (15 V) into another reactor.

10. Charged N-acetyl-L-tryptophan (2.83 g, 1.0 eq.) into the above reactor with stirring.

11. Charged DIC (1.45 g, 1.0 eq.), OxymaPure® (1.63 g, 1.0 eq.) and 2,4,6-collidine (1.82 g, 1.3 eq.) into the above reactor.

12. Cooled to below 10° C.

13. Charged Solution 1 slowly into the above reactor with stirring.

14. Warmed to room temperature slowly.

15. Stirred for 18 h at room temperature.

16. Sampled for IPC analysis—SM (N-acetyl-L-tryptophan): P=4.9%:67.1%].

17. Washed the reaction mixture with 1M KHSO$_4$ (3 V×1), water (3V×2) and brine (3 V×1).

18. Concentrated the organic phase under vacuum until no solvent left.

19. Slurry the residue with MTBE (20 V) for 1 h at room temperature.

20. Filtered and washed the solid with MTBE (3 V).

21. Collected the solid and dried.

22. Obtained 4.9 g yellow solid with 94.7% HPLC purity.

Process Description for Entry 6 of Table 5F

1. Charged Dimethylamine (2 M in THF, 120 mL, 4 V) into reactor.

2. Cooled to below 10° C.

3. Charged Compound 3 (30.0 g, 1.0 eq.) batchwise into reactor with stirring at below 10° C.

4. Stirred for 3 hours at 5±5° C.

5. Sampled for HPLC analysis (0.8% Compound 3 left, 270 nm).

6. Concentrated the mixture below 15° C. under vacuum until the residue 3-4 V left.

7. Switched the residue with DCM (5 V×3) until the residue 3-4 V left.

8. Diluted the residue with DCM (5 V)—obtained solution 1.

9. Charged DCM (600 mL, 20 V) into another 1 L reactor.

10. Charged N-acetyl-L-tryptophan (17 g, 1.0 eq.) into above 1 L reactor with stirring.

11. Cooled to below 10° C.

12. Charged OxymaPure® (9.8 g, 1.0 eq.), 2,4,6-collidine (10.9 g, 1.3 eq.) and solution 1 into the above 1 L reactor.

13. Finally charged EDC.HCl (13.2 g, 1.0 eq.) into the above 1 L reactor.

14. Stirred overnight at below 10° C.

15. Sampled for HPLC analysis (no Compound 4 left, SM:P=5.4%:91.6%, 270 nm).

16. Washed the above reaction mixture with water (5V×3).

17. Concentrated the organic phase under vacuum until the residue no more than 4 V left.

18. Switched the residue with EtOAc (5 V×3) until the residue was no more than 5 V left.

19. Slurry the residue overnight at room temperature.

20. Filtration and washed the solid with EtOAc (3-4 V).

21. Collected the solid and dried.

22. 18.5 g light yellow solid with 97.8% HPLC purity.

Example 6

Synthesis of Isopropyl (S)-2-((S)-2-acetamido-3-(1H-indol-3-yl)propanamido)-6-diazo-5-oxohexanoate (Compound 5) using propylphosphonic anhydride (T₃P®)

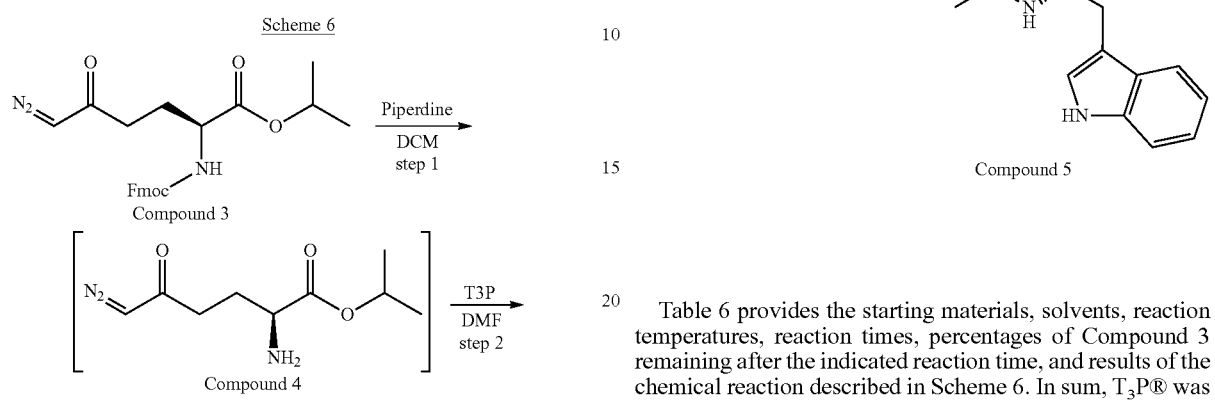

Scheme 6

Compound 5

Table 6 provides the starting materials, solvents, reaction temperatures, reaction times, percentages of Compound 3 remaining after the indicated reaction time, and results of the chemical reaction described in Scheme 6. In sum, T₃P® was not a suitable coupling agent for this reaction.

TABLE 3

| | Starting Materials | | | Reaction Conditions | | % Compound 2 remaining (HPLC) | |
|---|---|---|---|---|---|---|---|
| Entry | Compound 2 | TMSCHN₂ (2M in hexane) | n-BuLi (2.5M in hexane) | Temp (° C.) | Time (h) | | Result |
| 1 | 10 g (95%, 1.0 eq.) | 1.20 eq. | 1.23 eq. | −110 | 0.5 | 2~4% | 12.1 g light brown solid with 80% HPLC purity was obtained. Purification by column: from 5 g crude product, only obtained 1.3 g light yellow solid. |
| 2 | 10 g (95%, 1.0 eq.) | 1.23 eq. | 1.20 eq. | −110 | 0.5 | ~9% | Adding additional TMSCHN₂/n-BuLi, ~2% SM left. 12.5 g brown solid with 75% HPLC purity obtained |
| 3 | 10 g (95%, 1.0 eq.) | 1.20 eq. | 1.23 eq. | −75~−80 | 0.5 | ~2.3% | 8 g light brown solid with 88% HPLC purity was obtained via MTBE slurry. |
| 4 | 50 g (95%, 1.0 eq.) | 1.20 eq. | 1.23 eq. | −110 | 0.5 | ~3.6% | 44 g light brown solid with 81.8% HPLC purity was obtained via MTBE slurry. |
| 5 | 100 g (95%, 1.0 eq.) | 1.20 eq. | 1.23 eq. | −90~−80 | 0.25 | ~3.6% | 88.5 g light brown solid with 86.7% HPLC purity was obtained via MTBE slurry |
| 6 | 100 g (97%, 1.0 eq.) | 1.20 eq. | 1.23 eq. | −90~−80 | 0.25 | ~2.8% | 90.2 g light brown solid with 84.8% HPLC purity was obtained via MTBE slurry |
| 7 | 50 g (1.0 eq.) | 1.20 eq. (KF: 0.42%) | 1.23 eq. (Over 1 h) + 0.22 eq | −95~−85 | 0.5 | ~6.7% | 29.6 g of brown solid after drying. |

TABLE 4

| | Starting Materials | | | Reaction Conditions | | | |
|---|---|---|---|---|---|---|---|
| Entry | Compound 3 (HPLC purity 81%) | base | solvent | Temp (° C.) | Time (h) | HPLC | Result |
| 1 | 1.0 g (1.0 eq.) | TEA (2 V) | DCM (8 V) | 20-25 | 24 | No SM left | 9.7 g black sticky oil obtained, HNMR-assay only ~10%, and |
| 2 | 12.0 g (1.0 eq.) | TEA (3.5 eq.) | DCM (8 V) | 20-25 | 64 | No SM left | 0.58 g black crude product obtained after purification by column chromatography from 4.5 g crude oil |
| 3 | 0.2 g (1.0 eq.) | Piperidine (7.5 V) | DCM (7.5 V) | 15-20 | 3.5 | No SM left, HPLC content: 88.1% | N/A |
| | | | | | 22.5 | HPLC content: 71% | N/A |

TABLE 4-continued

| | Starting Materials | | | Reaction Conditions | | | |
|---|---|---|---|---|---|---|---|
| Entry | Compound 3 (HPLC purity 81%) | base | solvent | Temp (° C.) | Time (h) | HPLC | Result |
| 4 | 0.2 g (1.0 eq.) | Morpholine (7.5 V) | DCM (7.5 V) | 15-20 | 3.5 | trace SM left, HPLC content: 86.6% | N/A |
| | | | | | 22.5 | HPLCcontent: 63.5% | N/A |
| 5 | 0.2 g (1.0 eq.) | Ethanolamine (7.5 V) | DCM (7.5 V) | 15-20 | 3.5 | No SM left, HPLC content: 63% | N/A |
| 6 | 0.2 g (1.0 eq.) | TBAF (2.0 eq.) | DMF (10 V) | 15-20 | 3.5 | No SM left, but no product was detected | N/A |
| 7 | 0.2 g (1.0 eq.) | Cyclohexanamine (7.5 V) | DCM (7.5 V) | 15-20 | 3.5 | No SM left, HPLC content: 86.1% | N/A |
| | | | | | 22.5 | HPLC content: 71.0% | N/A |
| 8 | 0.2 g (1.0 eq.) | LiOH (1M, 2.0 eq.) | THF (10 V) | 15-20 | 3.5 | No SM left, but no product was detected | N/A |
| 9 | 2.0 g (1.0 eq.) | Cyclohexanamine (7.5 V) | DCM (7.5 V) | 15-20 | 1 | trace SM left | 0.6 g black oil obtained after purification by column (crude) |
| 10 | 5.0 g (1.0 eq.) | Morpholine (2.5 eq.) | DCM (7.5 V) | 15-20 | 3.5 | trace SM left | 40 g dark oil was obtained after work-up, but when after purification by column only bp 3 was detected |

TABLE 5A

| Step 1 | | | | | | | |
|---|---|---|---|---|---|---|---|
| | Starting Materials 1 | | | Reaction Conditions 1 | | | |
| Entry | Compound 3 | base | solvent | Temp (° C.) | Time (h) | HPLC | Result 1 |
| 1 | 5 g (1.0 eq.) | piperidine (2.5 eq.) | DCM (10 V) | 0-5 | 2 3 5 | ~17% Compound 3 left ~13% Compound 3left ~9% Compound 3 left | Telescoped to Step 2 |

| Step 2 | | | | | | | | |
|---|---|---|---|---|---|---|---|---|
| | Starting Materials 2 | | | | Reaction Conditions 2 | | | |
| | N-acetyl-L-tryptophan | add. | Oxyma pure | 2,4,6-collidine | solvent | Temp (° C.) | Time (h) | HPLC | Result 2 |
| | 3.5 eq. | DIC 3.5 eq. | 3.5 eq. | 4.55 eq. | DMF (20 V) | 10-20 | 2.5 18 | SM(acid):P = 33.1%:51.5% SM(acid):P = 28.4%:55.2% | Obtained 2.6 g brown solid with 89% HPLC purity by column purification from 32.88 g crude dark brown oil |

TABLE 5B

| Step 1 | | | | | | | |
|---|---|---|---|---|---|---|---|
| | Starting Materials 1 | | | Reaction Conditions 1 | | | |
| Entry | Compound 3 | base | solvent | Temp (° C.) | Time (h) | HPLC | Result 1 |
| 2 | 20 g (1.0 eq.) | piperidine (2.5 eq.) | DCM (8 V) | 5-15 | 3 4 | ~7% Compound 3 left ~4% Compound 3 left | Telescoped to Step 2 |

TABLE 5B-continued

Step 2

| Starting Materials 2 | | | | Reaction Conditions 2 | | | |
|---|---|---|---|---|---|---|---|
| N-acetyl-L-tryptophan | add. | Oxyma Pure ® | 2,4,6-collidine | solvent | Temp (° C.) | Time (h) | HPLC | Result 2 |
| 3.5 eq. | DIC 3.5 eq. | 3.5 eq. | 4.55 eq. | DMF (20 V) | 10-20 | 2 | SM(acid):P = 38.1%:51.6% | ~10.5 g brown solid with 82% HPLC purity by column purification |

TABLE 5C

Step 1

| Entry | Compound 3 | base | solvent | Temp (° C.) | Time (h) | HPLC | Result 1 |
|---|---|---|---|---|---|---|---|
| 3 | 130 g (1.0 eq.) | piperidine (2.5 eq.) | DCM (8 V) | 5-15 | 4 | ~4% Compound 3 left | Telescoped to Step 2 |

Step 2

| N-acetyl-L-tryptophan | add. | Oxyma Pure ® | 2,4,6-collidine | solvent | Temp (° C.) | Time (h) | HPLC | Result 2 |
|---|---|---|---|---|---|---|---|---|
| 3.5 eq. | DIC 3.5 eq. | 3.5 eq. | 4.55 eq. | DMF (20 V) | 10-20 | 2 | SM (acid): P = 42.4%:48.7% | 65 g yellow solid with more than 99% HPLC purity after purification by column |

TABLE 5D

Step 1

| Entry | Compound 3 | base | solvent | Temp (° C.) | Time (h) | HPLC | Result 1 |
|---|---|---|---|---|---|---|---|
| 4 | 5.0 g (1.0 eq.) | Diethylamine (3.5 V) | none | 5 ± 5 | 1 h | No Compound 3 left | Concentrated and switched with DCM, the residue was used directly to the next step |

Step 2

| N-acetyl-L-tryptophan | add | Oxyma Pure ® | 2,4,6-collidine | solvent | Temp (° C.) | Time (h) | HPLC | Result 2 |
|---|---|---|---|---|---|---|---|---|
| 2.83 g (1.0 eq.) | DIC 1.0 eq. | 1.0 eq. | 1.3 eq. | DCM (20 V) | RT | 18 h | SM(acid): P = 4.9%:67.1% | 4.9 g yellow solid via slurry with MTBE, HPLC purity 94.7% |

TABLE 5E

Step 1

| Entry | Starting Materials 1 | | | Reaction Conditions 1 | | | Result 1 |
|---|---|---|---|---|---|---|---|
| | Compound 3 | base | solvent | Temp (° C.) | Time (h) | HPLC | |
| 5 | 10.0 g purity: 90.9% (1.0 eq.) | Diethylamine (2M in THF, 4 V) | none | 5 ± 5 | 3 | Less than 2.0% Compound 3 left | Concentrated to less than 3 V left, and then switched with DCM(5 V × 3) to less than 3 V left, then diluted with DCM(5 V) (used directly to the next step) |

Step 2

| Starting Materials 2 | | | | Reaction Conditions 2 | | | Result 2 |
|---|---|---|---|---|---|---|---|
| N-acetyl-L-tryptophan | add | Oxyma Pure ® | 2,4,6-collidine | solvent | Temp (° C.) | Time (h) | HPLC | |
| 1.0 eq. | DIC 1.0 eq. | 1.0 eq. | 1.3 eq. | DCM (20 V) | 10-20 | overnight | No Compound 4 left, RCOOH:P = 5.3%:88.2%, Diastereomer: 0.6% | Not isolated |
| 1.0 eq. | EDC 1.0 eq. | 1.0 eq. | 1.3 eq. | DCM (20 V) | 10-20 | overnight | No Compound 4 left, RCOOH:P = 6.7%:88.9%, Diastereomer: 0.5% | 2.8 g light yellow solid; HPLC purity: 98.6% Two step yield: 60.6% |

TABLE 5F

| Entry | Step 1 | | | | | | |
|---|---|---|---|---|---|---|---|
| | Starting Materials 1 | | | Reaction Conditions 1 | | | Result 1 |
| | Compound 3 | base | solvent | Temp (° C.) | Time (h) | HPLC | |
| 6 | 30.0 g purity: 90.9% (1.0 eq.) | Diethylamine (2M in THF, 4 V) | none | 5 ± 5 | 3 | Less than 2.0% Compound 3 left | Concentrated to less than 3 V left, and then switched with DCM(5 V × 3) to less than 3 V left, then diluted with DCM(5 V) (used directly to the next step) |

Step 2

| Starting Materials 2 | | | | Reaction Conditions 2 | | | Result 2 |
|---|---|---|---|---|---|---|---|
| N-acetyl-L-tryptophan | add | Oxyma Pure ® | 2,4,6-collidine | solvent | Temp (° C.) | Time (h) | HPLC | |
| 1.0 eq. | EDC.HCl 1.0 eq. | 1.0 eq. | 1.3 eq. | DCM (20 V) | 10-20 | 14 | No Compound 4 left, RCOOH:P = 5.4%:91.6%, Diastereomer: 0.5% | 18.5 g light yellow solid; 97.8% HPLC purity Two step yield: 60.8% |

TABLE 6

| Entry | Step 1 | | | | | | |
|---|---|---|---|---|---|---|---|
| | Starting Materials 1 | | | Reaction Conditions 1 | | | |
| | Compound 3 | base | solvent | Temp (° C.) | Time (h) | HPLC | Result |
| 1 | 5 g (1.0 eq.) | piperidine (2.5 eq.) | DCM (10 V) | 15-20 | 2<br>3 | 3.1% Compound 3 left<br>1.5% Compound 3 left | Telescoped to Step 2 |

| | Step 2 | | | | | | |
|---|---|---|---|---|---|---|---|
| | Starting Materials 2 | | | Reaction Conditions 2 | | | |
| | N-acetyl-L-tryptophan | DIEA | T$_3$P ® (50% in EtOAc) | Temp (° C.) | Time (h) | HPLC | Result |
| | 3.5 eq. | 14.0 eq. | 5.3 eq. | 15-20 | 2.5<br>20 | Little product observed.<br>No obvious progress | N/A |

Example 7

Synthesis of Isopropyl (S)-2-((S)-2-acetamido-3-(1H-indol-3-yl)propanamido)-6-diazo-5-oxohexanoate (Compound 5)

Step 1: Synthesis of Compound 1

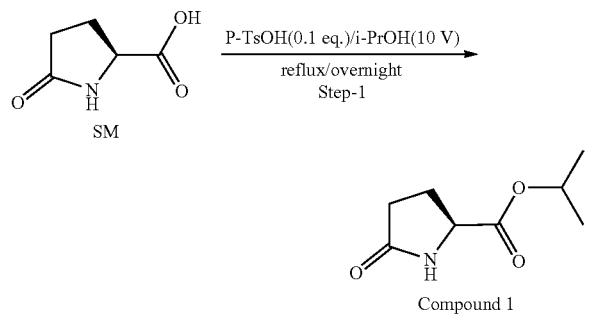

Process Description:
1. Charged propan-2-ol (10 L, 10 V) into a 20 L reactor under N$_2$ protection.
2. Charged (S)-5-oxopyrrolidine-2-carboxylic acid (1 Kg, 1.0 eq.) into reactor with stirring.
3. Charged 4-methylbenzenesulfonic acid (133.3 g, 0.1 eq.) into the above reactor.
4. Heated to reflux and stirred overnight at reflux.
5. Cooled to below 30° C.
6. Concentrated under vacuum to less than 1 V left.
7. Dissolved the residue with DCM (10 V)
8. Washed the organic phase with NaHCO$_3$ (sat., 3 V) and water (1.5 V) and brine (1.5 V).
9. Combined the aqueous phases in step 8 and extracted with DCM (5 V).
10. Washed the extraction with water (1 V) and brine (1 V).
11. Combined the organic phases in step 8 and step 10.
12. Concentrated the combined organic phase under vacuum to ~1 V left.
13. Charged n-heptane (3 V) into the residue with stirring.
14. Cooled to below 10° C. and stirred for at least 1 h at 0-10° C.
15. Filtered and washed the filter cake with n-heptane (0.5 V).
16. Obtained 580 g of product as a white solid after drying with high purity.
17. Concentrated the filtrate in step 15 under vacuum.
18. Dissolved the residue with DCM (10 V).
19. Washed the organic phase with NaHCO$_3$ (sat., 3 V) and water (1.5 V) and brine (1.5 V).
20. Combined the aqueous phases in step 19 and extracted with DCM (5 V).
21. Washed the extraction with water (1 V) and brine (1 V).
22. Combined the organic phases in step 19 and step 21.
23. Concentrated the combined organic phase under vacuum to ~1 V left.
24. Charged n-heptane (3 V) into the residue with stirring.
25. Cooled to below 10° C. and stirred for at least 1 h at 0-10° C.
26. Filtered and washed the filter cake with n-heptane (0.5 V).
27. Obtained another 440 g of product as a white solid after drying with high purity.
28. A total 1.02 Kg of Compound 1 was obtained as a white solid with 99.8% HPLC purity and 100% ee; yield: 76.9%.

Step 2: Synthesis of Compound 2

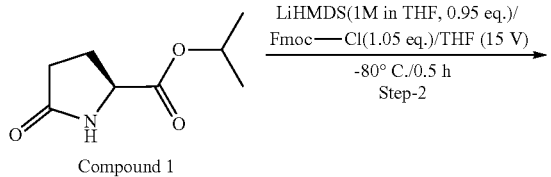

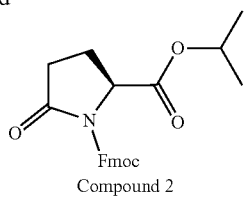

Compound 2

Process Description:
1. Charged THF (5 L, 10 V) into a 20 L reactor under $N_2$ protection.
2. Charged Compound 1 (500 g, 1.0 eq.) into reactor with stirring.
3. Cooled to below −80° C.
4. Charged dropwise a solution of LiHMDS (1 M in THF, 2.75 L, 0.95 eq.) into the above reactor while maintaining the temperature at −80±5° C.
5. Stirred for ~30 min at −80±5° C. (Solution 1).
6. Charged dropwise a solution of Fmoc-Cl (795 g, 1.05 eq.) in THF (2.5 L, 5 V) into solution 1 with stirring at −80±5° C.
7. Stirred for 30 min at −80±5° C.
8. Sampled for IPC (no Compound 1 left).
9. Charged water (3.75 L, 7.5 V) and AcOH (2.0 eq.) into another 20 L reactor.
10. Cooled to 0° C. with stirring (solution 2).
11. Transferred the reaction mixture (solution 1) into the above solution (solution 2) with stirring under $N_2$ press while maintaining the temperature at 0±5° C.
12. Warmed to 10~15° C.
13. Phase separated and collected the above organic phase.
14. Washed the organic phase two times with half sat. brine (5 V).
15. The same reaction was repeated 2 times on the same scale, and the organics after washing were combined for further solidification.
16. Concentrated the combined organic phase under vacuum until the residue had no more than 5 V left.
17. Switched the residue two times with IPA (5 V) under vacuum until the residue had no more than 8 V left.
18. Stirred for 2-3 h at 25~30° C.
19. Filtered and washed the solid with IPA (3 V).
20. Collected the solid and dried.
21. 2.06 Kg of Compound 2 was obtained as a white solid with high purity and 100% ee, yield: 89.6%.

Step 3. Synthesis of Compound 3

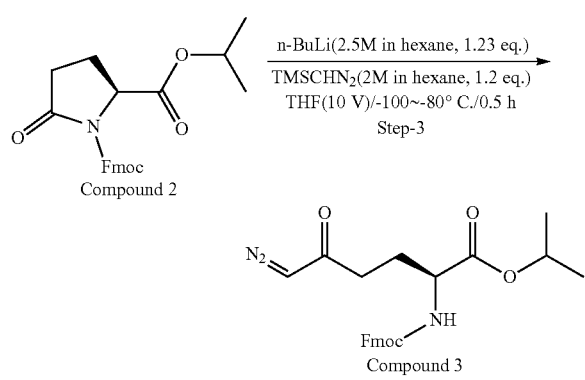

Process Description:
1. Charged THF (12 L, 10 V) into a 20 L reactor under $N_2$ protection.
2. Charged Compound 2 (1.2 Kg, 1.0 eq.) into reactor with stirring.
3. Cooled to ~−70° C.
4. Charged $TMSCHN_2$ (2 M in hexane, 1.83 L, 1.20 eq.) into the above mixture while maintaining the temperature at below −60° C.
5. Cooled to ~−90° C.
6. Charged dropwise n-BuLi (2.5 M in n-hexane, 1.5 L, 1.23 eq.) into the above reaction mixture while maintaining the temperature at −90±10° C. (over ~2 h).
7. Stirred for 0.5 h at −90±10° C.
8. Sampled for IPC 1 (Area % of Compound 2).
9. Quenched the reaction by charging acetic acid (225.3 g, 1.23 eq. (1.0 eq. of n-BuLi)) dropwise into the above reaction mixture while maintaining the temperature at below −80° C. (over ~0.5 h).
10. Warmed to 0° C. (over ~2 h).
11. Charged dropwise 20% aq. $NH_4Cl$ solution (5.0 w/w) into the above reaction mixture while maintaining the temperature at 0~5° C. (over ~1 h).
12. Warmed to 25±5° C.
13. Stirred for ~1.5 h at 25±5° C.
14. Sampled for IPC 2 (Area % of Compound 3-INT (Silyl ether): 1.1%).
15. Phase separated and collected the organic phase.
16. Washed the organic phase two times with 12.5% brine (5 V).
17. Transferred the organic phase into the concentrating reactor via a microporous filter (0.22 μm) under vacuum.
18. Concentrated the organic phase to 2.5~3.0 V left under vacuum while maintaining the temperature at below 35° C.
19. Adjusted the temperature to 20~25° C.
20. Charged dropwise n-heptane (20 V) into the residue over ~3.5 h at 20±5° C.
21. Stirred for ~6 h at 20±5° C.
22. Centrifuged.
23. Washed the cake with n-heptane (5 V).
24. Sampled the cake for HPLC analysis (Area % of Compound 3: 89.2%).
25. Dissolved the above cake in DCM (2 V/the cake).
26. Adjusted the temperature to 2025° C. and stirred untile the solid dissolved completely.
27. Charged dropwise n-heptane (18 V/the cake) over ~4 h to the residue at 20±5° C.
28. Stirred for ~6 h at 20±5° C.
29. Centrifuged.
30. Washed the second cake with n-heptane (4 V/the first cake).
31. Sampled the second cake for HPLC analysis (Area % of Compound 3: 94.7%).
32. Dried the solid under vacuum at 20~25° C. for 6 h.
33. Sampled the solid for LOD analysis (LOD: 1.7%).
34. Packaged the solid in double LDPE bags and then packaged in aluminium foil bag.

35. 0.82 Kg of Compound 3 was obtained as light brown solid with 94.7% HPLC purity and 100% ee, yield: 61.7%, and stored at −20±5° C. under protection from light.

Step 4: Synthesis of Compound 4

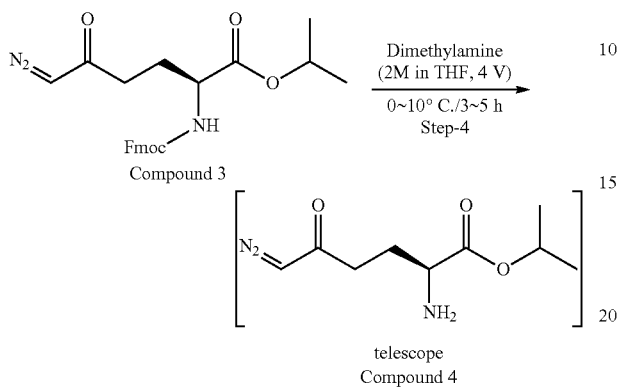

telescope
Compound 4

Process Description:
1. Charged dimethylamine (2 M in THF, 6.6 L, 4 V) into reactor (without N$_2$ protection).
2. Cooled to below 5° C. with stirring.
3. Portionwise charged Compound 3 (1.65 Kg, 1.0 eq.) into reactor while maintaining the temperature at below 10° C.
4. Stirred for ~4 hours at 5±5° C.
5. Sampled for HPLC analysis (Area % of Compound 3: 4.8% (270 nm).
6. Charged dimethylamine (2 M in THF, 0.32 L, 0.2 V) into reactor.
7. Stirred for an additional 1 hour at 5±5° C.
8. Sampled for HPLC analysis (Area % of Compound 3: 2.7% (270 nm).
9. Charged Dimethylamine (2 M in THF, 0.18 L, 0.1 V) into reactor.
10. Stirred for an additional 1 hour at 5±5° C.
11. Sampled for HPLC analysis (Area % of Compound 3: 1.6% (270 nm).
12. Concentrated the reaction mixture under vacuum while maintaining the temperature at below 20° C. until the residue 2~3 V left.
13. Switched the residue three times with DCM (5 V) under vacuum while maintaining the temperature at below 20° C. until the residue 2~3 V left.
14. Diluted the residue with DCM (5 V).
15. Obtained "Compound 4 in DCM solution" amd stored below 0° C. for direct use in the next step.

Step 5: Synthesis of Compound 5

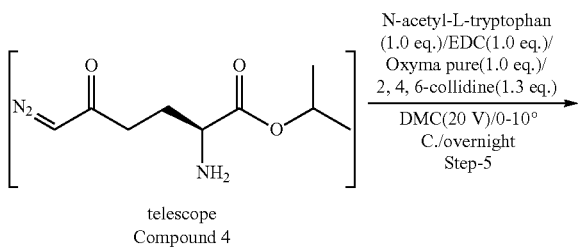

telescope
Compound 4

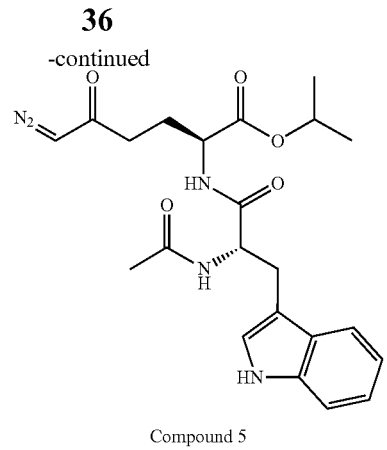

Compound 5

Process Description:
1. Charged DCM (33 L, 20 V/Compound 3) into a 100 L reactor under N$_2$ protection.
2. Charged N-acetyl-L-tryptophan (0.93 Kg, 1.0 eq./Compound 3) into reactor with stirring.
3. Cooled to below 5° C.
4. Charged OxymaPure® (0.54 Kg, 1.0 eq./Compound 3) into the above reactor.
5. Charged 2,4,6-collidine (0.6 Kg, 1.3 eq./Compound 3) into the above reactor.
6. Charged the "Compound 4 in DCM solution" from Step 4 into the above reactor.
7. Charged EDC (0.73 Kg, 1.0 eq./Compound 3) into the above reactor.
8. Stirred ~8 hours at 0~10° C.
9. Sampled for HPLC analysis (Area % of Compound 4: 0.2% (270 nm)).
10. Washed the above reaction mixture three times with sterile water for injection (5 V).
11. Concentrated the organic phase under vacuum while maintaining the temperature at below 40° C. until the residue was 3~4 V left.
12. Switched the residue three times with EtOAc (5 V) while maintaining the temperature at below 40° C. until the residue was 3~4 V left.
13. Charged EtOAc (5 V) into the residue and the slurry was stirred for 5 h at 20±5° C.
14. Centrifuged for the first time.
15. Washed the cake with EtOAc (3 V).
16. Re-slurried the wet cake with EtOAc (5 V/the cake) for 4 h at 20±5° C.
17. Centrifuged for the second time.
18. Washed the second cake with EtOAc (3 V/the first cake).
19. 0.85 Kg of a wet cake of Compound 5 was obtained as a light brown solid with 98.5% HPLC purity was obtained (the area % of an impurity (RRT: 1.17%) was 0.57%.
20. Dissolved the wet cake of step 19 in a mixture solution of DCM (6 L, 7 V/the wet cake) and MeOH (3.4 L, 4 V/the wet cake) at 20±5° C.
21. Charged silica gel (100~200 mesh, 1.5 w/the wet cake) into the above solution and stirred for 5-10 min.
22. Concentrated the system under vacuum while maintaining the temperature at below 40° C. until there was no distillate out.
23. Charged silica gel (100~200 mesh, 15 w/the wet cake) into a column.
24. Charged the silica gel solid with the product into the column.

25. Purified the crude product by column chromatography using MeOH in DCM (1% to 2%, w/w) as the eluent, collected the eluent every 10~15 V and sampled for HPLC analysis. Collected and combined the eluent which the area % of Compound 5 was ≥98.0% and the area % of the impurity (RRT:0.92)≤1.0% and the area % of other single impurity ≤0.5%.

26. Concentrated the combined eluent under vacuum to 2.0~3.0 V/the wet cake left while maintaining the temperature at below 40° C.

27. Switched the residue three times with EtOAc (3.0 V/the wet cake) to 2.0~3.0 V/the wet cake left while maintaining the temperature at below 40° C.

28. Adjusted the temperature to 20±5° C.

29. Charged EtOAc (3.0 V/the wet cake) to the reactor and the slurry was stirred for 3 hours at 20±5° C.

30. Centrifuged.

31. Washed the third cake with EtOAc (2.0 V/the second cake).

32. Sampled the cake for HPLC analysis (Area % of Compound 5:99.5%, the area % of the impurity (RRT:0.92): 0.18%, and area % of all the other impurities <0.5%).

32. Dried the solid under vacuum for 6 hours at 25±5° C.

33. Sampled for LOD analysis (LOD: 0.36%).

34. Packaged the solid in double LDPE bags and then package in aluminium foil bag.

35. 603 g of Compound 5 was obtained as a light brown solid in 100% ee, yield: 36% over two steps. The product was stored at −20±5° C. under protection from light.

Step 6: Recrystallization of Compound 5

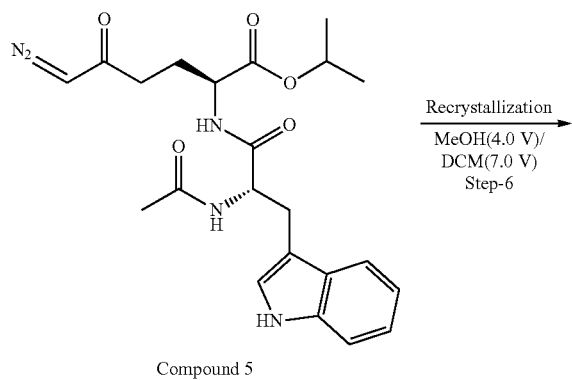

Compound 5

Recrystallization
MeOH(4.0 V)/
DCM(7.0 V)
Step-6

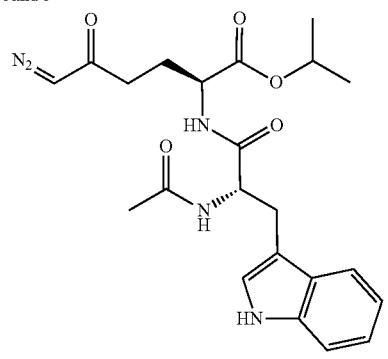

Compound 5

Process Description:

1. Charged DCM (7 V) into a 20 L reactor under $N_2$ protection.

2. Adjusted the temperature to 20±5° C. with stirring.

3. Charged Compound 5 from Step 5 (566 g, 1.0 w/w) into the reactor.

4. Charged MeOH (4 V) into the above reactor and the solution was stirred to a clear solution at 20±5° C.

5. Transferred the above solution into a 10 L reactor via a sterile microporous filter (0.2 μm) under vacuum.

6. Concentrated the solution under vacuum to 2.0~3.0 V left while maintaining the temperature at below 40° C.

7. Charged DCM (1.75 V) and MeOH (1.0 V) into the above 20 L reactor and stirred to a clear solution.

8. Transferred the above solution into the 10 L reactor via the sterile microporous filter.

10. Concentrated the solution in the 10 L reactor under vacuum to 2.0~3.0 V left while maintaining the temperature at below 40° C.

11. Switched the residue three times with EtOAc (5 V, filter via the sterile microporous filter) under vacuum to 2.0~3.0 V left while maintaining the temperature at below 40° C.

12. Charged EtOAc (5 V, filter via the sterile microporous filter) into the residue.

13. Adjusted the temperature to 20±5° C.

14. Slurried for 3-4 h at 20±5° C.

15. Filtered and washed the solid with EtOAC (3 V, filter via the sterile microporous filter).

16. Collected the solid and dried under vacuum for 6 hours at 20-30° C.

17. Sampled the solid for LOD and then solvent residual and then HPLC and crystal form analysis.

18. Packaged the solid in double sterile bags and then package in aluminium foil bag.

Figure 7:
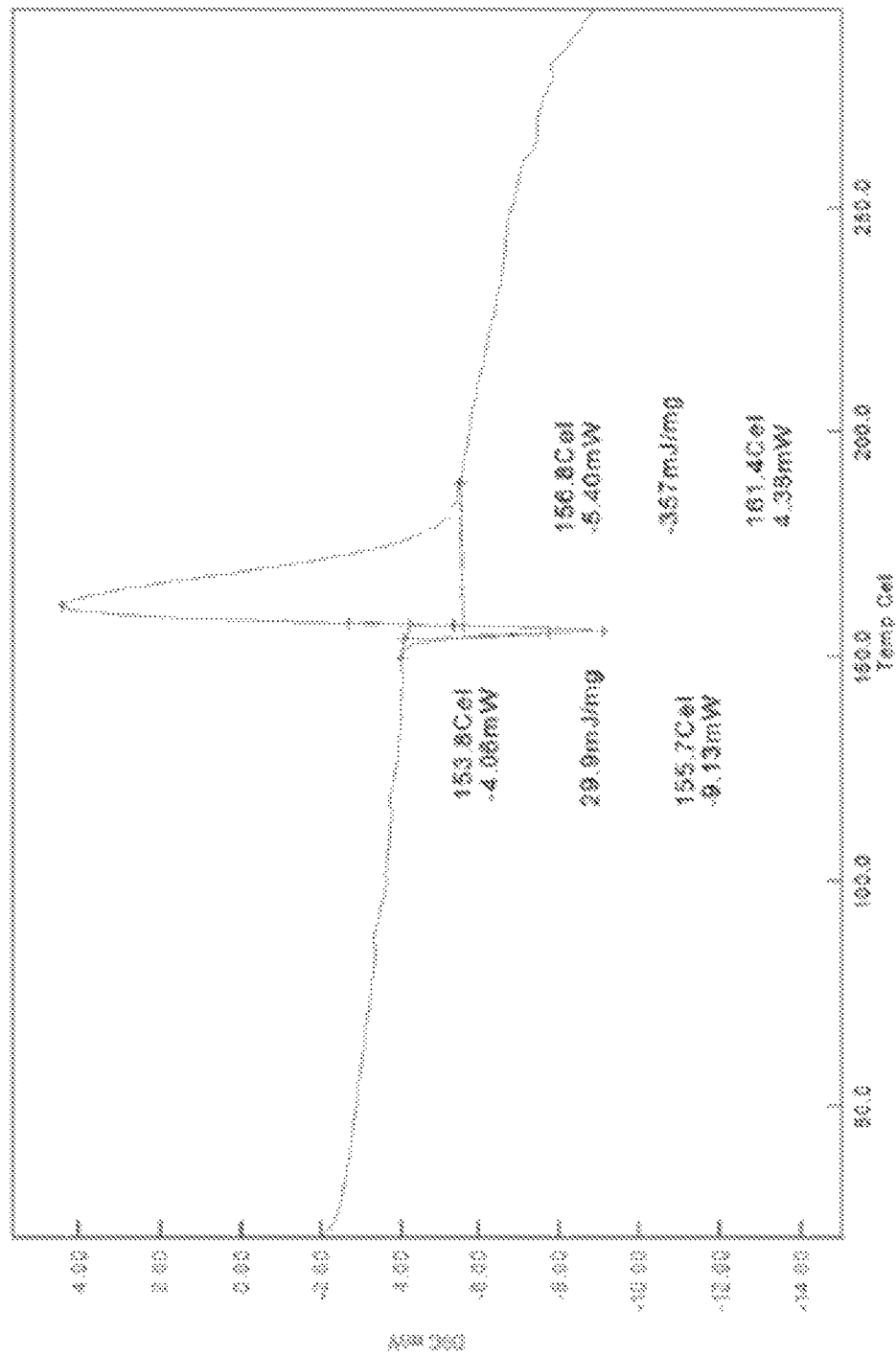
FIG. 7 is a DCS thermogram of Compound 5 ((isopropyl (S)-2-((S)-2-acetamido-3-(1H-indol-3-yl)propanamido)-6-diazo-5-oxohexanoate).
Figure 8:
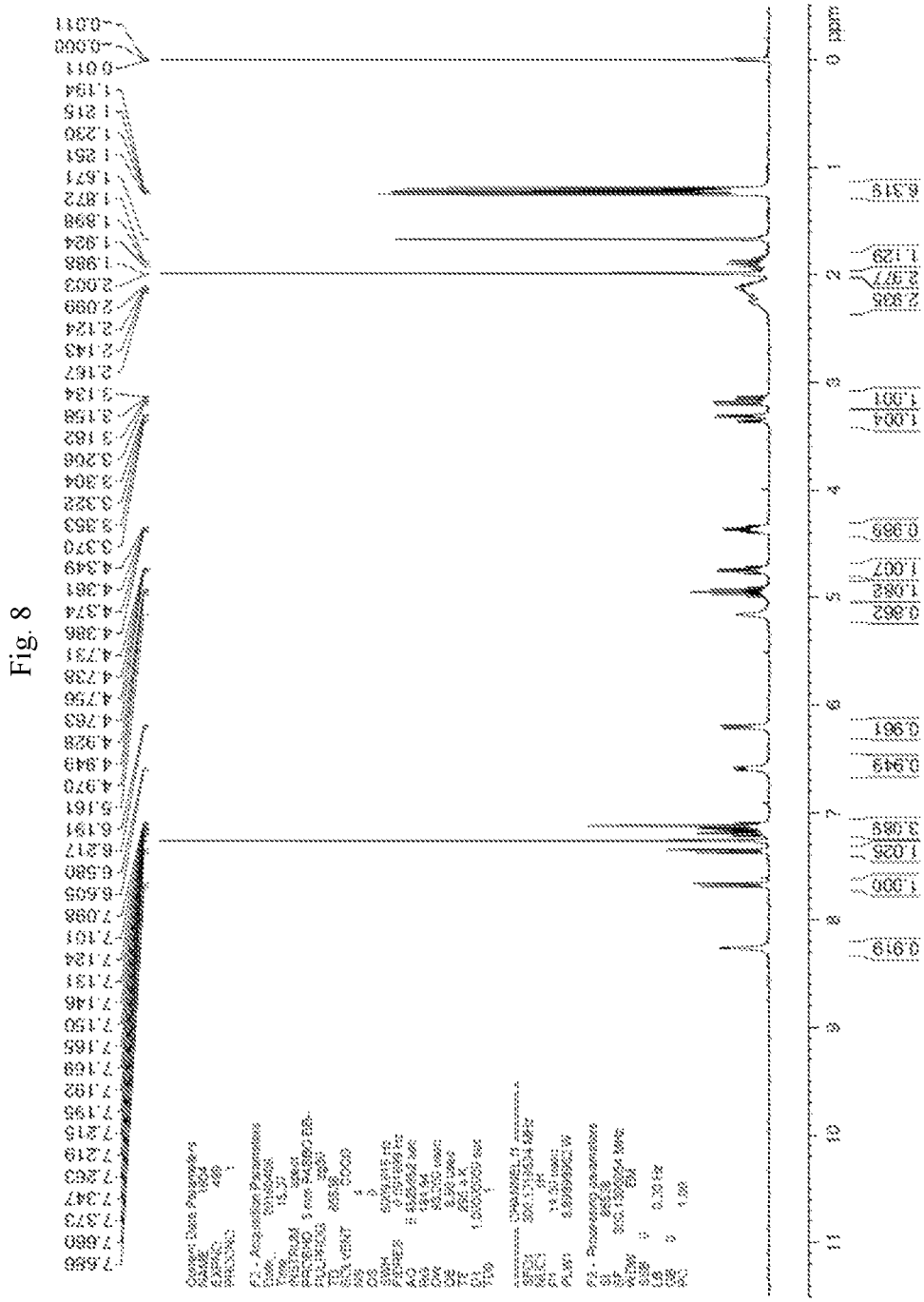
FIG. 8 is a $^1$H NMR spectrum of Compound 5 ((isopropyl (S)-2-((S)-2-acetamido-3-(1H-indol-3-yl)propanamido)-6-diazo-5-oxohexanoate).

19. 461.6 g of Compound 5 was obtained as light yellow crystalline solid: yield: 81.4%; HPLC purity: >99%, ee: ee: 100%. The product was stored at −20±5° C. under protection from light. The XRPD diffractogram of Compound 5 is provided in FIG. 6, and the peak list is provided in Table 7. DSC analysis (FIG. 5) showed an endotherm at onset 154° C. (peak at 156° C.) and exotherm at onset 157° C. (peak at 161° C.). The DCS thermogram of Compound 5 is provided in FIG. 7. The $^1$H NMR of Compound 5 is provided in FIG. 8.

TABLE 7

| Pos. [°2θ] | Height [cts] | d-spacing [Å] | Rel. Int. [%] |
| --- | --- | --- | --- |
| 3.3147 | 726.36 | 26.65517 | 10.57 |
| 6.6267 | 6870.51 | 13.32775 | 100.00 |
| 9.9541 | 192.09 | 8.88620 | 2.80 |
| 13.2973 | 1139.22 | 6.65861 | 16.58 |
| 16.6286 | 83.82 | 5.33140 | 1.22 |
| 18.2795 | 847.47 | 4.84943 | 12.33 |
| 19.9539 | 1693.71 | 4.44613 | 24.65 |
| 20.3647 | 571.69 | 4.35735 | 8.32 |
| 21.5792 | 494.13 | 4.11819 | 7.19 |
| 23.3773 | 705.13 | 3.80534 | 10.26 |
| 25.8218 | 1203.58 | 3.45037 | 17.52 |
| 28.4378 | 64.58 | 3.13865 | 0.94 |
| 30.2311 | 129.88 | 2.95643 | 1.89 |
| 33.6991 | 91.14 | 2.65969 | 1.33 |

X-ray Powder Diffraction (XRPD) analysis was carried out on a PANalytical X'pert pro, scanning the samples between 3 and 35° 2θ. The material was loaded onto a multi-well plate with Kapton or Mylar polymer film to support the sample. The multi-well plate was then placed into the diffractometer and analysed using Cu K radiation (α1λ=1.54060 A; α2=1.54443 A; β=1.39225 A; α1:α2 ratio=0.5) running in transmission mode (step size 0.0130° 2θ) using 40 kV/40 mA generator settings.

Differential Scanning Calorimetry (DSC) analysis was carried out on a Seiko DSC6200 (equipped with a cooler) cooled and held at 20° C. Once a stable heat-flow response was obtained, the sample and reference were heated to 320° C. at a scan rate of 10° C./min and the resulting heat flow response monitored. Nitrogen was used as the purge gas, at a flow rate of 50 cm3/min.

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

What is claimed is:

1. A method of preparing a compound of Formula I:

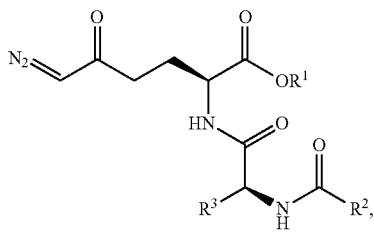

the method comprising:
(a) reacting a compound of Formula II:

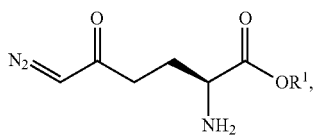

with a compound of Formula III:

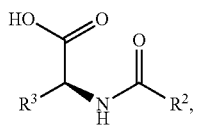

in a solvent in the presence of an alkyl cyano(hydroxyimino)acetate, a carbodiimide, and a base at a temperature of about 0° C. to about 40° C., wherein:
$R^1$ is $C_1$-$C_4$ alkyl;
$R^2$ is $C_1$-$C_4$ alkyl; and
$R^3$ is selected from the group consisting of $C_1$-$C_6$ alkyl, (aryl)alkyl, and (heteroaryl)alkyl; and
(b) isolating the compound of Formula I.

2. The method of claim 1, wherein the solvent is selected from the group consisting of N,N-dimethylformamide, N-methyl-2-pyrrolidinone, dimethylacetamide, dichloromethane, tetrahydrofuran, 2-methyltetrahydrofuran, and dioxane.

3. The method of claim 1, wherein the carbodiimide is N,N'-diisopropylcarbodiimide or N,N'-dicyclohexylcarbodiimide.

4. The method of claim 1, wherein the alkyl cyano(hydroxyimino)acetate is ethyl cyano(hydroxyimino)acetate.

5. The method of claim 1, wherein the stereomutation of a compound having Formula II is less than about 2% and the stereomutation of a compound having Formula III is less than about 2%.

6. The method of claim 1, wherein the compound of Formula II is obtained by reacting a compound of Formula IV:

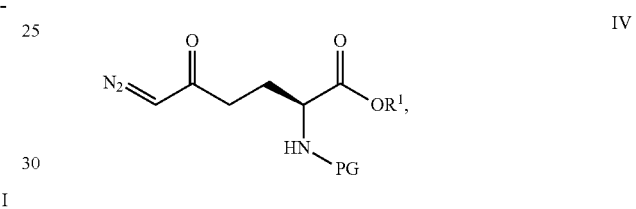

with a deprotecting agent in a solvent at a temperature of about −5° C. to about 30° C., wherein:
$R^1$ is $C_1$-$C_4$ alkyl; and
PG is a protecting group.

7. The method of claim 6, wherein PG is selected from the group consisting of fluorenylmethyloxycarbonyl, carboxybenzyl, tert-butyloxycarbonyl, allyloxycarbonyl, and methyl carbamate.

8. The method of claim 6, wherein the compound of Formula IV is obtained by reacting a compound of Formula V:

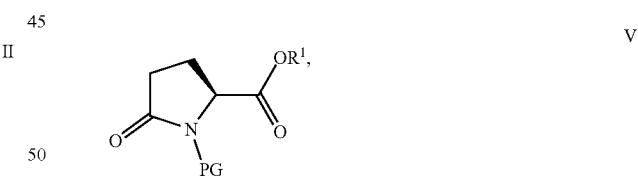

with a diazo reagent in the presence of an organolithium reagent in a solvent at a temperature of about −120° C. to about −40° C.,
wherein:
$R^1$ is $C_1$-$C_4$ alkyl; and
PG is a protecting group.

9. The method of claim 8, wherein PG is selected from the group consisting of fluorenylmethyloxycarbonyl, carboxybenzyl, and tert-butyloxycarbonyl.

10. The method of claim 8, wherein the diazo reagent is trimethylsilyldiazomethane and the organolithium reagent is n-butyllithium.

11. The method of claim 8, wherein the compound of Formula V is obtained by reacting a compound of Formula VI:

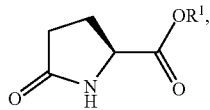

with compound of Formula VII:

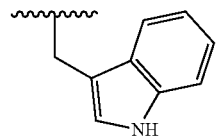

in a solvent at a temperature of about −100° C. to about −60° C.,
wherein:
$R^1$ is $C_1$-$C_4$ alkyl;
X is selected from the group consisting of —Cl, —Br, —I, —O-succinimide, —O-1,2,3-benzotriazole, and —O-aryl; and
PG is a protecting group.

12. The method of claim 11, wherein PG is fluorenylmethyloxycarbonyl, carboxybenzyl, or tert-butyloxycarbonyl.

13. The method of claim 11, wherein the compound of Formula VI is obtained by esterifying L-pyroglutamic acid with $R^1$OH, wherein $R^1$ is $C_1$-$C_4$ alkyl.

14. The method of claim 1, wherein $R^1$ is isopropyl.

15. The method of claim 1, wherein $R^2$ is methyl.

16. The method of claim 1, wherein $R^3$ is:

17. The method of claim 1, wherein isopropyl (S)-2-((S)-2-acetamido-3-(1H-indol-3-yl)propanamido)-6-diazo-5-oxohexanoate is obtained in about 35-90% yield or more starting from a compound of Formula II.

18. The method of claim 1, wherein isopropyl (S)-2-((S)-2-acetamido-3-(1H-indol-3-yl)propanamido)-6-diazo-5-oxohexanoate is obtained in about 98% chemical purity or more starting from a compound of Formula II.

19. The method of claim 1, wherein isopropyl (S)-2-((S)-2-acetamido-3-(1H-indol-3-yl)propanamido)-6-diazo-5-oxohexanoate is obtained in about 98% ee or more starting from a compound of Formula II.

20. Crystalline (S)-2-((S)-2-acetamido-3-(1H-indol-3-yl)propanamido)-6-diazo-5-oxohexanoate characterized as having powder x-ray diffraction peaks at 6.6, 13.3, 18.3, 20.0, 23.4, and 25.8 degrees 2Θ.

\* \* \* \* \*